US006287767B1

(12) United States Patent
Bronstein et al.

(10) Patent No.: US 6,287,767 B1
(45) Date of Patent: *Sep. 11, 2001

(54) CHEMILUMINESCENT ENERGY TRANSFER ASSAYS

(75) Inventors: Irena Bronstein, Newton; Brooks Edwards, Cambridge; John Voyta, Sudmary, all of MA (US)

(73) Assignee: Tropix, Inc., Bedford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/190,181

(22) Filed: Nov. 12, 1998

Related U.S. Application Data

(63) Continuation of application No. 08/811,539, filed on Mar. 4, 1997, now Pat. No. 5,849,495, which is a continuation of application No. 08/401,285, filed on Mar. 9, 1995, now Pat. No. 5,753,436, which is a continuation of application No. 08/172,277, filed on Dec. 23, 1993, now abandoned.

(51) Int. Cl.[7] ............................................... G01N 33/53
(52) U.S. Cl. ............... 435/6; 435/7.4; 435/7.9; 435/7.92; 435/7.21; 435/966; 435/968; 435/975; 549/221; 549/214; 556/405; 558/86; 558/99; 558/167; 558/184; 558/193; 558/197
(58) Field of Search ................. 435/6, 7.4, 7.9, 435/7.92, 7.21, 968, 966, 975; 549/221, 214, 332, 510; 536/18.1; 556/405; 558/86, 99, 167, 184, 193, 197; 560/139, 144; 564/269; 568/326, 633

(56) References Cited

U.S. PATENT DOCUMENTS

| | | | |
|---|---|---|---|
| 4,956,477 | * 9/1990 | Bronstein et al. | 549/221 |
| 4,978,614 | * 12/1990 | Bronstein et al. | 435/21 |
| 5,004,565 | 4/1991 | Schaap . | |
| 5,112,960 | * 5/1992 | Bronstein et al. | 536/18.1 |
| 5,177,241 | 1/1993 | Bronstein et al. . | |
| 5,225,584 | 7/1993 | Brooks et al. . | |
| 5,336,596 | * 8/1994 | Bronstein et al. | 435/6 |
| 5,362,916 | 11/1994 | Edwards et al. . | |
| 5,538,847 | * 7/1996 | Bronstein et al. | 435/6 |
| 5,582,980 | * 12/1996 | Bronstein et al. | 435/6 |
| 5,625,077 | 4/1997 | Bronstein . | |
| 5,637,747 | 6/1997 | Bronstein et al. . | |
| 5,639,907 | 6/1997 | Bronstein et al. . | |
| 5,648,555 | 7/1997 | Bronstein et al. . | |
| 5,679,802 | 10/1997 | Bronstein et al. . | |
| 5,679,803 | * 10/1997 | Bronstein et al. | 549/220 |
| 5,756,770 | 5/1998 | Bronstein et al. . | |
| 5,763,681 | 6/1998 | Edwards et al. . | |
| 5,777,133 | 7/1998 | Bronstein et al. . | |
| 5,840,919 | * 11/1998 | Bronstein et al. | 549/220 |
| 5,851,771 | * 12/1998 | Bronstein et al. | 435/6 |
| 5,856,522 | 1/1999 | Bronstein et al. . | |

FOREIGN PATENT DOCUMENTS

03053897 A2 * 3/1991 (JP) .

OTHER PUBLICATIONS

R.J. Cano, et al., Detection of Salmonellas by DNA Hybridization with a Fluorescent Alkaline Phosphatase Substrate, Journal of Applied Bacteriology, 1992, 72:393–399.

Ramon A. Evangelista, et al., Alkyl– and Aryl–Substituted Salicyl Phosphates as Detection Reagents in Enzyme–Amplified Fluorescence DNA Hybridization Assays on Solid Support, Analytical Biochemistry 1992 203:218–226.

I. Bronstien, et al., Improved Chemiluminescent Western Blotting Procedure, Product Application Focus, vol. 12, No. 5 (1992).

\* cited by examiner

*Primary Examiner*—Bennett Celsa
(74) *Attorney, Agent, or Firm*—Piper Marbury Rudnick & Wolfe LLP; Steven B. Kelber

(57) ABSTRACT

A chemiluminescent assays for the determination of the presence or amount of a biopolymer in bound assays using 1,2-dioxetanes in connection with AttoPhos™ as chemiluminescent substrates for enzyme-labeled targets or probes is provided. Further disclosed is a kit for conducting a bioassay for the presence or concentration of a biopolymer comprising a) an enzyme complex; b) a 1,2-dioxetane; and c) AttoPhos™.

4 Claims, 22 Drawing Sheets

CHEMILUMINESCENT ENERGY TRANSFER ASSAYS

This application is a continuation of U.S. patent application Ser. No. 08/811,539, filed on Mar. 4, 1997, now U.S. Pat. No. 5,849,495, issued Dec. 15, 1998 which is a continuation of U.S. patent application Ser. No. 08/401,285, filed on Mar. 9, 1995, now U.S. Pat. No. 5,753,436, issued May 19, 1988 which is a continuation of U.S. patent application Ser. No. 08/172,277, filed on Dec. 23, 1993, now abandoned.

FIELD OF THE INVENTION

This invention relates to the energy transfer chemiluminescent assays for the determination of the presence or amount of a biological substance in surface-bound assays using 1,2-dioxetanes in connection with hydrophobic fluorometric substrates such as AttoPhos™ as chemiluminescent substrates for enzyme-labeled fluorometric substrate targets or probes. The chemiluminescence of the dioxetane donor-AttoPhos™ acceptor substrate pair can be enhanced by the addition of a polymeric enhancer. Further enhancement can be achieved by adding, in sequence, AttoPhos™ and then the 1,2-dioxetane.

BACKGROUND OF THE INVENTION

Chemiluminescent assays for the detection of the presence or concentration of a biological substance have received increasing attention in recent years as a fast, sensitive and easily read method of conducting bioassays. In such assays, a chemiluminescent compound is used as a reporter molecule, the reporter molecule chemiluminescing in response to the presence or the absence of the suspected biopolymer.

A wide variety of chemiluminescent compounds have been identified for use as reporter molecules. One class of compounds receiving particular attention is the 1,2-dioxetanes. 1,2-dioxetanes can be stabilized by the addition of a stabilizing group to at least one of the carbon atoms of the dioxetane ring. An exemplary stabilizing group is spiro-bound adamantane. Such dioxetanes can be further substituted at the other carbon position with an aryl moiety, preferably phenyl or naphthyl, the aryl moiety being substituted by an oxygen which is, in turn, bound to an enzyme-labile group. When contacted by an enzyme capable of cleaving the labile group, the oxyanion of the dioxetane is formed, leading to decomposition of the dioxetane and spontaneous chemiluminescence. A wide variety of such dioxetanes are disclosed in U.S. Pat. No. 5,112,960. That patent focuses on dioxetanes which bear a substituent on the adamantyl-stabilizing group, such as halo substituents, alkyl groups, alkoxy groups and the like. Such dioxetanes represent an advance over earlier-recognized dioxetanes, such as 3-(4-methoxyspiro[1,2-dioxetane-3,2'-tricyclo]-3.3.1.1$^{3,7}$] decan]-4-yl) phenyl phosphate, and in particular, the disodium salt thereof, generally identified as AMPPD®. The chlorine-substituted counterpart, which converts the stabilizing adamantyl group from a passive group which allows the decomposition reaction to go forward, to an active group which gives rise to enhanced chemiluminescence signal due to faster decomposition of the dioxetane anion, greater signal-to-noise values and better sensitivity, is referred to as CSPD®. Other dioxetanes, such as the phenyloxy-β-D-galactopyranoside (AMPGD) are also well-known, and can be used as reporter molecules. These dioxetanes, and their preparation, do not constitute an aspect of the invention herein, per se.

Assays employing these dioxetanes can include conventional assays, such as Southern, Northern and Western blot assays, DNA sequencing, ELISA, as well as other liquid phase and mixed phase assays performed on membranes and beads. In general, procedures are performed according to standard, well-known protocols except for the detection step. In DNA assays, the target biological substance is bound by a DNA probe with an enzyme covalently or indirectly linked thereto, the probe being admixed with the sample immobilized on a membrane, to permit hybridization. Thereafter, excess enzyme complex is removed, and dioxetane added to the hybridized sample. If hybridization has occurred, the dioxetane will be activated by the bound enzyme, leading to decomposition of the dioxetane, and chemiluminescence. In solution-phase assays, the enzyme is frequently conjugated to a nucleic acid probe or immune complexed with an antibody responsive to the target biological substance, unbound components being removed, and the dioxetane added, chemiluminescence being produced by the decomposition of the dioxetane activated by the amount of enzyme present. In cases where the enzyme itself is the target, the dioxetane need only be added to the sample. Again, a wide variety of assay modalities has been developed, as disclosed in U.S. Pat. No. 5,112,960, as well as U.S. Pat. No. 4,978,614.

It has been well-known that light-quenching reactions will occur if the dioxetane decomposition occurs in a protic solvent, such as water. As the samples suspected of containing or lacking the analyte in question are generally biological samples, these assays generally take place in an aqueous environment. The light-quenching reactions therefor may substantially reduce the chemiluminescence actually observed from the decomposition of the dioxetane. In assays involving low-level detections of particular analytes, such as nucleic acids, viral antibodies and other proteins, particularly those prepared in solution or in solution-solid phase systems, the reduced chemiluminescence observed, coupled with unavoidable background signals, may reduce the sensitivity of the assay such that extremely low levels of biological substances cannot be detected. One method of addressing this problem is the addition of water-soluble macromolecules, which may include both natural and synthetic molecules, as is disclosed in detail in U.S. Pat. No. 5,145,772. The disclosure of this patent is incorporated herein, by reference. To similar effect, U.S. Pat. No. 4,978,614 addresses the addition of various water-soluble "enhancement" agents to the sample, although the patent speaks to the problem of suppressing non-specific binding reactions in solid state assays. In U.S. Pat. No. 5,112,960, preferred water-soluble polymeric quaternary ammonium salts such as poly(vinylbenzyltrimethylammonium chloride) (TMQ) poly(vinylbenzyltributylammonium chloride) (TBQ) and poly(vinylbenzyldimethylbenzylammonium chloride) (BDMQ) are identified as water-soluble polymeric quaternary ammonium salts which enhance chemiluminescence and provide greater sensitivity by increasing the signal-to-noise ratio. Similar phosphonium and sulfonium polymeric salts are also disclosed.

This enhancement is achieved, at least in part, through the formation of hydrophobic regions in which the dioxetane oxyanion is sequestered. Decomposition in these hydrophobic regions enhances chemiluminescence, because water-based light quenching reactions are suppressed. Among the recognized water-soluble quaternary polymer salts employed, TBQ provides unexpectedly superior enhancement, through this hydrophobic region-forming mechanism.

The chemiluminescent enhancement achieved by the addition of water-soluble polymeric substances such as ammonium, phosphonium and sulfonium polymeric salts can be further improved by the inclusion, in the aqueous sample, of an additive, which improves the ability of the quaternary polymeric salt to sequester the dioxetane oxyanion and the resulting excited state emitter reporting molecule in a hydrophobic region. Thus, the combination of the polymeric quaternary salt and the additive, together, produce an increase in enhancement far beyond that produced separately by the addition of the polymeric quaternary salt, or the additive, which, when a surfactant or water-soluble polymer itself, may enhance chemiluminescence to a limited degree. The synergistic combination of the polymeric quaternary salt and additives gives enhancement effects making low-level, reliable detection possible even in aqueous samples through the use of 1,2-dioxetanes. The polymeric quaternary salts, coupled with the additives, are sufficiently powerful enhancers to show dramatic 4 and 5-fold increases at levels below 0.005 percent down to 0.001 percent. Increased signal, and improved signal/noise ratios are achieved by the addition of further amounts of the polymeric quaternary salt, the additive, or both, in amounts up to as large as 50 percent or more. In general, levels for both polymeric quaternary salt and additive can be preferably within the range of 0.01–25 percent, more preferably from 0.025–15 percent by weight. The details of this improvement are disclosed in U.S. application Ser. No. 08/031,471 which issued as U.S. Pat. No. 5,547,836 on Aug. 20, 1996 which is incorporated herein by reference.

U.S. Pat. No. 5,208,148 describes a class of fluorescent substrates for detection of cells producing the glycosidase enzyme. The substrate is a fluorescein diglycoside which is a non-fluorescent substrate until hydrolyzed by glycosidase enzyme inside a cell to yield a fluorescent detection product excitable between about 460 nm and 550 nm. The fluorescent enzymatic hydrolysis products are specifically formed and adequately retained inside living cells, and are non-toxic to the cells. The substrates can penetrate the cell membrane under physiological conditions. Therefore, the invention permits analysis, sorting and cloning of the cells and monitoring of cell development in-vitro and in-vivo. However, these fluorescent products are detected in the single cells and within specific organelles of single cells only after the spectral properties of the substrates are excited by an argon laser at its principle wavelengths.

Known fluorescent emitters have been used with dioxetanes in bioassays. U.S. Pat. Nos. 4,959,182 and 5,004,565 describe methods and compositions for energy transfer enhancement of chemiluminescence from 1,2-dioxetanes. These patents utilize a fluorescent micelle comprising a surfactant and a fluorescent co-surfactant which exists in the bulk phase of the buffer solution used. The fluorescent co-surfactant is present in a form capable of energy transfer-based fluorescence at all times. In contact with a solid phase containing an enzyme-labeled ligand binding pair, the fluorescent moiety tends to remain associated with the micelle in the bulk phase. If any fluorescent co-surfactant is deposited on the solid phase, this occurs indiscriminately, in areas containing the immobilized ligand binding pair, and in areas which do not contain said pair. Thus a problem results in that the fluorescent emitters never are, or do not remain associated with the immobilized enzyme conjugate. Thus the close proximity needed for energy transfer from the dioxetane to the fluorescent emitter is not efficient. Further because the fluorescent emitters can be deposited anywhere on the solid phase matrix, this method does not allow for specificity when used in bound assay. The majority of the examples in the '182 and '565 patents are solution phase enzyme assays or chemical triggering experiments not utilizing enzymes. These examples are better matched to the bulk phase co-micelle as a means to promote the proximity of the dioxetane anion product with the energy accepting fluorescent surfactant. The only example of a solid phase assay occurs at columns 29 and 30. This ELISA assay shows that light is produced on a well surface over the range of 112 ng to 1.3 ng of S-antigen. However, there are no control experiments showing light production from the same dose-response experiment, but using dioxetane and CTAB surfactant in the absence of fluorescent co-surfactant. Thus one cannot determine how efficient the energy transfer at the solid surface actually is. Certainly, however, this fluorescent co-surfactant is not a non-fluorescent enzyme substrate such as AttoPhos™. Thus the present invention, wherein a fluorescent energy acceptor is produced directly, and locally on a surface, by the same enzyme which catalytically decomposes the dioxetane energy donor, is not suggested by these art references.

There are several basic problems which relate to fluorescent substrates used in surface or blotting experiments. One is that the excitation of the dephosphorylated chromophore has to be performed with a laser or a lamp with a filter or a monochromator. These light sources are not only cumbersome, but increase the expense of the assay. This necessary and key excitation step which is accomplished with UV/blue light results in a second problem which is autofluorescence of the membrane or surface and other solid supports which ordinarily contain fluorescent brighteners and other excitable fluorophores, as well as exciting chromophores contained in the biological sample (i.e., proteins and nucleic acids). Such fluorescent signal of the surface or membrane support and sources other than the dephosphorylated or activated substrate, contribute to unacceptable levels of background which substantially lower the sensitivity and specificity of the assay so that substrates such as these cannot be used.

Known fluorescent emitters have been used with dioxetanes in nonbound assays. However, a problem results in that the fluorescent emitters don't stay associated with the enzyme conjugate. Therefore, the close proximity needed for the energy transfer from the dioxetane to the fluorescent emitter is not possible. Further, because the fluorescent emitters don't stay associated with the enzyme conjugate, the emitters do not allow for specificity when used in bound assays.

Therefore, notwithstanding the advances in chemiluminescence technology addressed by the above assays, it remains a goal of the industry to provide chemiluminescent assays providing overall more intense signals, thus having greater sensitivity and specificity without the use of expensive, cumbersome lasers or lamps, to determine the presence, concentration or both of a biological substance in a sample. 1,2-dioxetane compounds have already been developed which show excellent potential as reporter molecules for such chemiluminescent assays. However, it is still necessary to improve upon the sensitivity and specificity of the chemiluminescence of the 1,2-dioxetane molecules by providing an efficient fluorescent acceptor emitter which stays in close contact with the dioxetane to thereby allow for the necessary energy transfer, and further, to allow for sensitive and specific determination of the target.

SUMMARY OF THE INVENTION

Therefore, it is an object of the present invention to provide a method for determining the presence or amount of a biological substance in biological surface-bound and solution-phase assays using 1,2-dioxetane donor molecules in combination with a fluorescent acceptor emitter, which provides increased sensitivity or signal-to-noise ratio without the use of any outside light sources for excitation.

The above objects have been met by the present invention which provides a method for determining the presence or the amount of a biological substance in a biological sample, wherein the method comprises the steps of: a) forming an enzyme conjugated binder (antibody or DNA probe) with the biological ligand from the sample; b) adding a hydrophobic fluorometric substrate such as AttoPhos™ and a 1,2-dioxetane to the bound enzyme conjugated binder; c) wherein the enzyme of the enzyme conjugated biopolymer cleaves an enzyme cleavable group such as a phosphate moiety from the AttoPhos™ and from the dioxetane causing the dioxetane to decompose through an excited state emitter form such that energy transfer occurs from the excited state chemiluminescent emitter to the dephosphorylated AttoPhos™, causing this moiety to emit; and d) determining the presence or amount of the biological substance as a function of the amount of fluorescence.

The objects have further been met by the present invention which further provides a kit for conducting a bioassay for the presence or concentration of a biological substance which is detected either bound to a surface or in a solution assay, said kit comprising: a) an enzyme complex which will stably bind to a surface-bound biological substance; b) a 1,2-dioxetane which when contacted by the enzyme complex will be caused to decompose into a decomposition product which is capable of transferring its energy; and c) AttoPhos™.

DETAILED DESCRIPTION OF DRAWINGS

FIG. 1 is an illustration of the method of the present invention showing the energy transfer from CSPD® to dephosphorylated Atto, thereby releasing energy in the form of fluorescence.

FIG. 2 (A)–(D) is a CCD image of Western blot analysis of rabbit IgG on Nitrocellulose Membrane. A detailed description of FIG. 2 can be found in Example 1.

FIG. 3 is a graph of a Western blot analysis of rabbit IgG on Nitrocellulose Membrane showing chemiluminescent intensity (average and maximum).

FIGS. 4(A)–(D) is a CCD image of Western blot analysis of rabbit IgG on PVDF membrane. FIG. 4 is specifically explained in Example 1.

FIG. 5 is a graph of a Western blot analysis of rabbit IgG on PVDF membrane showing chemiluminescent intensity (average and maximum).

FIGS. 6(A)–(B) are graphs of PSA (Prostate Specific Antigen), ng/mL versus RLU, 5 sec of chemiluminescent detection of PSA comparison of CSPD to CSPD®+ AttoPhos™.

DETAILED DESCRIPTION OF THE INVENTION

Figure 1:
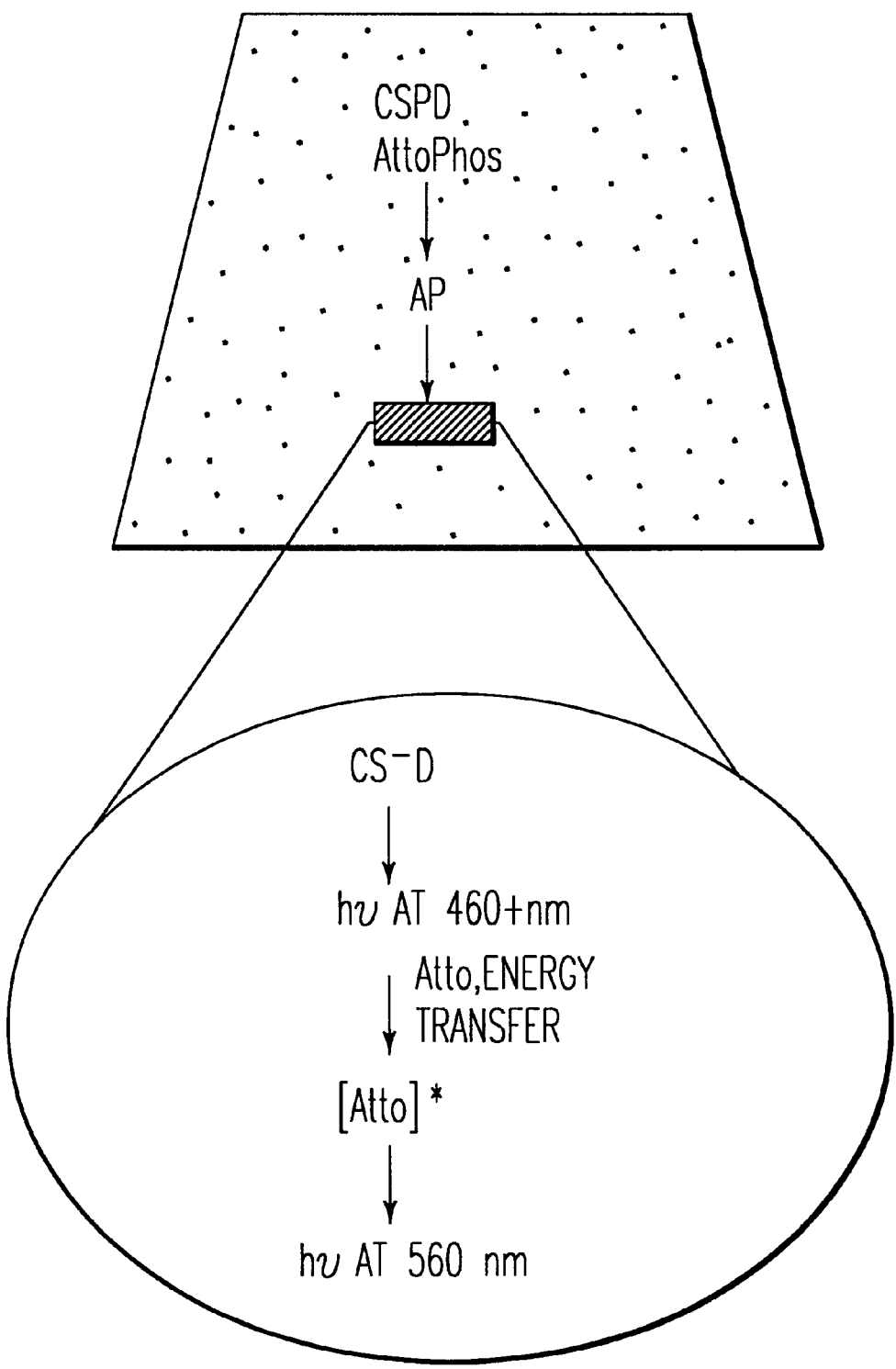
Figure 2A:
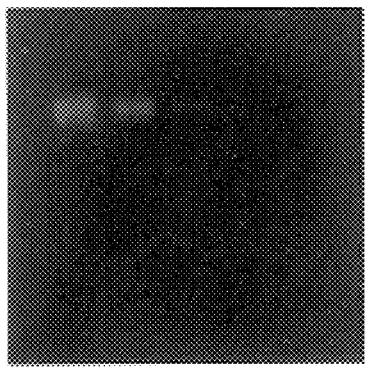
Figure 2B:
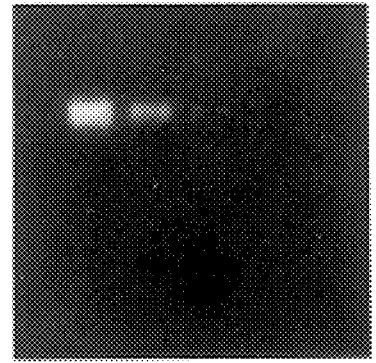
Figure 2C:
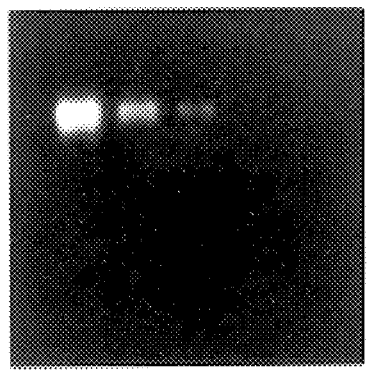
Figure 2D:
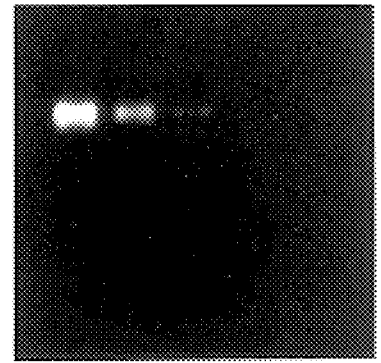

The present invention will now be described more fully hereinafter with references to the accompanying drawings, in which preferred embodiments of the invention are shown. This invention can, however, be embodied in many different forms and should not be construed as limited to the embodiments set forth herein; rather, Applicant provides these embodiments so that this disclosure will be thorough and complete, and will fully convey the scope of the invention to those skilled in the art. It should be noted that the fluorometric substrate is not specifically limited, save for hydrophobicity, discussed below. Exemplary substrates are disclosed in U.S. Pat. No. 5,208,148 incorporated herein by reference.

This invention makes use of a hydrophobic fluorometric substrate. By this is intended a compound which upon activation by an enzyme can be induced to emit in response to energy transfer from an excited state dioxetane decomposition product donor. As the donor is hydrophobic, the substrate, when activated, must be sufficiently hydrophobic as to be sequestered in the same hydrophobic regions to which the donor migrates, for energy and transfer to occur.

The present invention is described in terms of a method for determining the presence or amount of a substance or determined in a solution-phase assay biological substance using 1,2-dioxetanes using the hydrophobic fluorometric substrate AttoPhos™. The kit of the present invention also for determining the presence or amount of a substance, is described using a suitable enzyme conjugate, a 1,2-dioxetane and AttoPhos™. Other fluorometric substrates may be used.

The present inventors have found for the first time that 1,2-dioxetane in connection with AttoPhos™ improves both the specificity and sensitivity of surface-bound assays. Further, these assays using 1,2-dioxetane in connection with AttoPhos™ alleviate the need for light sources necessary for excitation.

Specifically, the present invention uses the high quantum yield of fluorescence, affinity for surfaces possessed by AttoPhos™, coupled with the enzyme activated chemiluminescence of 1,2-dioxetane as the excitation source for the dephosphorylated AttoPhos™. Thus, dephosphorylated AttoPhos™ is produced at the surface and stays in close proximity with the enzyme environment throughout the assay, and the excitation of the acceptor—dephosphorylated AttoPhos™ can be performed without any external instrumentation and without possible excitation of chromophores which are other than the dephosphorylated AttoPhos™.

The method can be used for determining the presence or the amount of a biological substance in a biological sample. The method comprises the steps of: a) forming an enzyme conjugated binder (antibody or nucleic acid probe) complex with a biological substance from the biological sample; b) adding AttoPhos™ and a 1,2-dioxetane to the bound enzyme conjugate biological substance complex; c) wherein the enzyme of the enzyme conjugate cleaves a phosphate moiety from the AttoPhos™ and from the dioxetane, thereby causing the dioxetane to decompose through an excited state form such that an energy transfer occurs from the excited state donor of dioxetane to the dephosphorylated AttoPhos™ acceptor, causing it to luminesce; and d) determining the presence or amount of the biological substance as a function of the amount of luminescence.

The kit of the present invention is also for determining the presence or concentration of a biopolymer and comprises: a) an enzyme complex which will bind to a biological substance upon admixture therewith; b) a 1,2-dioxetane which when contacted by the enzyme of the enzyme complex will be caused to decompose into a decomposition product which is in an excited state; and c) AttoPhos™.

The assays and kits of this invention employ water-soluble chemiluminescent 1,2-dioxetanes. As noted above, these dioxetanes are well established in the art, and their identity and preparation do not constitute a novel aspect of this invention, per se. In general, any chemiluminescent dioxetane which exhibits sufficient solubility and stability in aqueous buffers to conduct the assay, and which may be caused to decompose and chemiluminesce by interaction with an enzyme, and cleavage, by the enzyme, of an enzyme labile group inducing the decomposition, can be used in connection with this invention.

Typically, the 1,2-dioxetanes useful in this invention will have the general formula:

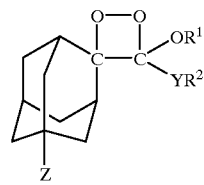

(I)

wherein
Z=H, Cl, other halogens, alkyl, carboxy, or alkoxy groups;
$R^1$ is $C_1$–$C_{20}$ alkyl or $C_{1-12}$ aryl or aralkyl;
Y is phenyl or naphthyl, unsubstituted or substituted with an electron donating or electron withdrawing group;
$R^2$ is meta-substituted or non-conjugated on Y with respect to the dioxetane, and is OX, wherein;
X is an enzyme cleavable group which, when cleaved, leaves the dioxetane phenoxy or naphthoxy anion.

Suitable dioxetanes are those disclosed in U.S. Pat. application 08/057,903, which is now U.S. Pat. No. 5,538,847, the entire disclosure of which is incorporated herein by reference. Preferred dioxetanes include dioxetanes in which X is a phosphate moiety. Particularly preferred dioxetanes include AMPPD®, and in particular, its disodium salt, as well as CSPD®, and in particular, its disodium salt. Methods of preparing these dioxetanes are disclosed in the aforereferenced, commonly-assigned patents, as well as, e.g., U.S. Pat. No. 4,857,652, assigned to Wayne State University. The preparation, purification and isolation of the dioxetanes does not constitute a novel aspect of the invention disclosed and claimed herein per se.

AttoPhos™ is a highly sensitive fluorometric substrate for the detection of alkaline phosphatase. The chemical structure of AttoPhos™ is not known at the present time. However, the chemical properties of AttoPhos™ are known. AttoPhos™ was developed by JBL-Scientific and can be obtained from the JBL-Scientific catalog (1993) at catalog number 1670A.

The chemical and physical properties of AttoPhos™ are as follows. AttoPhos™ is a pale, yellow crystalline solid having a molecular weight of approximately 580 grams/mol. The turnover number for AttoPhos™ is 85,400 molecules of AttoPhos™ per minute per molecule of alkaline phosphatase in 2.40 M DEA (diethanolamine) pH 9.0, 0.23 mM $MgCl_2$ and 0.005% NaN, by weight. The solubility of AttoPhos™ is ≧10 mM in aqueous 2.4 M DEA buffer at a pH of 9.0. The optimum alkaline phosphatase turnover occurs at a substrate concentration of 0.5–1.5 mM AttoPhos™. AttoPhos™ has a Km value of 0.030 mM and a molar absorptivity of 31.412.

When contacted with alkaline phosphatase, AttoPhos™ is known to become a fluorescent emitter. The molecular weight of the fluorescent emitter is approximately 290 g/mole. This fluorescent emitter has an excitation maximum in the visible range at 430–450 nm with fluorescence monitored at 550–570 nm, in a DEA buffer. Best conditions are at 440 nm for excitation with 550 nm emission. The fluorescent emitter also has an emission maximum at 560 nm, and a large Stokes Shift of 140 nm. The Water Raman emission occurs at 470 nm with an excitation at 413 nm. The fluorescent emitter has a maximum at 418 nm with a coefficient of 26,484 in 0.392 M $Na_2CO_3$ and a pH of 11.0 and is fully ionized at a pH>10.0.

The dioxetane is added to an enzyme complex which is bound to a biological binder (antibody or nucleic probe).

The enzyme complex is also bound to the target biological substance. The dioxetane is therefore the substrate for the enzyme, the enzyme-catalyzed cleavage of the labile groups of the substrate form the body of the dioxetane resulting in the formation of the unstable oxyanion, and subsequent decomposition of the dioxetane. The enzyme is usually complexed with a binder moiety, such as a DNA probe in a hybridization step or suitable antibody in an incubation step, so as to help bind to the biological substance.

The hybridization step can be carried out using standard, well-known procedures and using a suitable probe.

As an alternative to a hybridization step, an incubation step can be carried out in the usual manner using a suitable antibody.

The enzyme conjugate can be any enzyme conjugate capable of stably binding to the biological substance. Examples of the enzyme conjugate are any ligand-binder pair, probe with a covalently attached enzyme, or antibody labeled directly with alkaline phosphatase. Alternatively, the nucleic acid probes and antibodies may be labelled indirectly with enzymes via a biotin-[strept]avidin or antigen-antibody (such as degoxigenin-antidigoxigenin, fluorescein-antifluorescein) and other type coupling. Derivatized alkaline phosphatases such as Streptavidin-alkaline phosphatase alkaline phosphatase labeled antibodies and DNA probes, are the preferred enzyme conjugates useful in the present invention.

After the enzyme conjugate-biological substance complex is formed; AttoPhos™ and the 1,2-dioxetane are added to the bound enzyme conjugate complexed with biological substance either simultaneously, or AttoPhos™ is added first, allowed to dephosphorylate, and subsequently, a 1,2-dioxetane is added.

It will be apparent to those of skill in the art that it is the process of enzyme cleavage which places the energy-donating dioxetane emitter fragment in close proximity to Atto™ which is also produced locally by the same enzyme. Attophos™ itself, like other fluorometric enzyme substrates is non-fluorescent in the bulk phase. Thus, any non-enzymatic decomposition of the dioxetane, which would produce a noise signal, is not amplified by energy transfer in the bulk phase. Thus it is an enzyme reaction which produces the hydrophobic, fluorescent form allowing immobilization on the surface used to perform the assay. It will also be apparent that other hydrophobic, fluorimetric enzyme substrates can also be used in the invention. U.S. Pat. No. 5,208,148, referred to above, describes fluorescein diglycosides which are specifically modified by the inclusion of a range of hydrophobic moieties attached to the planar, fluorophore itself. Such hydrophobic substrates. would be useful for performing the bioassays of the invention where the enzyme label utilized is a glycosidase such as beta-galactosidase and the dioxetane was of the general structure shown above where for example, Z=Cl, $R^1$=methyl, Y=phenylene, and X=beta-D-galactopyranoside. Of course, the hydrophobic hydroxyfluoresceins shown in this patent as precursors to the diglycosides may instead by phosphorylated using known art to give hydrophobic fluorescein mono- and diphosphate derivatives which are useful in the present invention.

The enzyme cleaves a phosphate moiety from both the 1,2-dioxetane and AttoPhos™. As the 1,2-dioxetane becomes dephosphorylated by the enzyme, the formed oxyanion becomes the excited state donor, and its energy is transferred to the closely positioned acceptor—the dephosphorylated Attophos™ emitter, causing it to emit. FIG. 1 illustrates the energy transfer from the 1,2-dioxetane (CSPD®) to the dephosphorylated AttoPhos™, which in turn, releasing energy in the form of luminescence. The energy transfer efficiency is enhanced as the dephosphorylated product of AttoPhos™—the acceptor, is hydrophobic and is immobilized in the surface/biological substance sites and therefore is in very close proximity to the chemiluminescent dephosphorylated 1,2-dioxetane's excited state fragment which is the energy donor.

The 1,2-dioxetane is added to the bound enzyme conjugate complexed with biological substance in an amount of from 0.01 to 2.5 mM, preferably 0.25 to 1 mM. Most preferably, the 1,2-dioxetane is ed in an amount of 0.25 mM.

AttoPhos™ in the 2.40 M diethanolamine (DEA) in water buffer is added to the enzyme or enzyme conjugated binder complexed with biological substance in an amount of from 1–100%, preferably 25 to 75% by volume. Most preferably, 10 to 50% by volume AttoPhos™ is added.

As stated above, it is preferred that Attophos™ is added first, allowed to dephosphorylate, and subsequently, a 1,2-dioxetane is added. The time period between addition of AttoPhos™ and addition of a 1,2-dioxetane is preferably 10 to 60 minutes, more preferably 20 to 40 minutes, and most preferably 25 to 30 minutes. The signal can be further enhanced by the addition of a water-soluble macromolecule along with Attophos™ or other hydrophic fluorometric enzyme substrate. Preferred water-soluble polymers useful in practicing the invention, are based, in general, on polymeric onium salts, particularly quaternary salts based on phosphonium, sulfonium and, preferably, ammonium moieties. The polymers have the general formula I shown below:

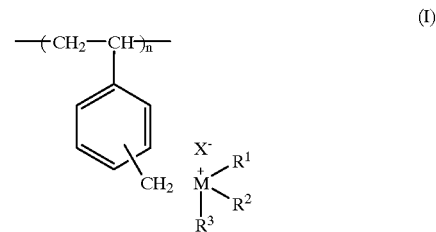

(I)

In this formula each of $R^1$, $R^2$ and $R^3$ can be a straight or branched chain unsubstituted alkyl group having from 1 to 20 carbon atoms, inclusive, e.g., methyl, ethyl, n-butyl, t-butyl, hexyl, or the like; a straight or branched chain alkyl group having from 1 to 20 carbon atoms, inclusive, substituted with one or more hydroxy, alkoxy, e.g., methoxy, ethoxy, benzyloxy or polyoxethylethoxy, aryloxy, e.g., phenoxy, amino or substituted amino, e.g., methylamino, amido, e.g., acetamido or ureido, e.g., phenyl ureido; or fluoroalkane or fluoroaryl, e.g., heptafluorobutyl, groups, an unsubstituted monocycloalkyl group having from 3 to 12 carbon ring carbon atoms, inclusive, e.g., cyclohexyl or cyclooctyl, a substituted monocycloalkyl group having from 3 to 12 ring carbon atoms, inclusive, substituted with one or more alkyl, alkoxy or fused benzo groups, e.g., methoxycyclohexyl or 1,2,3,4-tetrahydronaphthyl, a polycycloalkyl group having 2 or more fused rings, each having from 5 to 12 carbon atoms, inclusive, unsubstituted or substituted with one or more alkyl, alkoxy or aryl groups, e.g., 1-adamantyl or 3-phenyl-1-adamantyl, an aryl, alkaryl or aralkyl group having at least one ring and from 6 to 20 carbon atoms in toto, unsubstituted or substituted with one or more alkyl, aryl, fluorine or hydroxy groups, e.g., phenyl, naphthyl, pentafluorophenyl, ethylphenyl, benzyl, hydroxybenzyl, phenylbenzyl or dehydroabietyl; at least two of $R_1$, $R_2$ and $R_3$, together with the quaternary nitrogen atom to which they are bonded, can form a saturated or unsaturated, unsubstituted or substituted nitrogen-containing, phosphorus-containing or sulfur-containing ring having from 3 to 5 carbon atoms, inclusive, and 1 to 3 heteroatoms, inclusive, and which may be benzoannulated, e.g., 1-pyridinium, 1-(3-alkyl or aralkyl)imidazolium, morpholino, alkyl morpholinium, alkylpiperidinium, N-acylpiperidinium, piperidino or acylpiperidino, benzoxazolium, benzthiazolium or benzamidazolium.

The symbol $X^-$ represents a counterion which can include, alone or in combination, moieties such as halide, i.e., fluoride, chloride, bromide or iodide, sulfate, alkylsulfonate, e.g., methylsulfonate, arylsulfonate, e.g., p-toluenesulfonate, substituted arylsulfonate, e.g., anilinonaphthylenesulfonate (various isomers), diphenylanthracenesulfonate, perchlorate, alkanoate, e.g., acetate, arylcarboxylate, e.g., fluorescein or fluorescein derivatives, benzoheterocyclic arylcarboxylate, e.g., 7-diethylamino-4-cyanocoumarin-3-carboxylate, organic dianions such as p-terephthalate may also be represented by $X^-$.

The symbol n represents a number such that the molecular weight of such poly(vinylbenzyl quaternary salts) will range from about 800 to about 200,000 (weight average), and preferably from about 20,000 to about 70,000, as determined by intrinsic viscosity or LALLS techniques.

Methods for the preparation of these polymers, related copolymers and the related starting materials where M is nitrogen are disclosed in G. D. Jones et al, *Journal of Polymer Science*, 25, 201, 1958; in U.S. Pat. Nos. 2,780,604; 3,178,396; 3,770,439; 4,308,335; 4,340,522; 4,424,326 and German Offenlegunsschrift 2,447,611.

The symbol M may also represent phosphorous or sulfur whereupon the corresponding sulfonium or phosphonium polymers have been described in the prior art: U.S. Pat. Nos. 3,236,820 and 3,065,272.

Methods of preparation of the two polymers of this invention are set forth in the referenced U.S. Patents, and do not constitute any aspect of this invention, per se.

Copolymers containing 2 or more different pendant onium groups may also be utilized in the invention described herein:

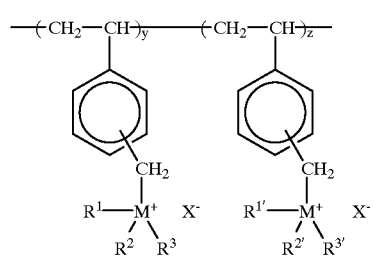

II

The symbols X, M', $R^{1'}$, $R^{2'}$, $R^{3'}$ are as described above for X, M, $R^1$–$R^3$. The symbols Y and Z represent the individual monomers comprising the copolymer. The symbols Y and Z may thus individually vary from 0.01 to 0.99, with the sum always equalling one.

As preferred moieties, M is N or P, and $R^1$–$R^3$ are individually, independently, alkyl, cycloalkyl, polycycloalkyl (e.g. adamantane) aralkyl or aryl, having 1 to 20 carbon atoms, unsubstituted or further substituted with hydroxyl, amino, amido, ureido groups, or combine to form via a Spiro linkage to the M atom a heterocyclic (aromatic, aliphatic or mixed, optionally including other N, S or O hetero atoms) onium moiety.

X is preferably selected to improve solubility and to change ionic strength as desired, and is preferably halogen, a sulfate, a sulfonate. In copolymers, each of $R^1$–$R^3$ may be the same as or different from the corresponding $R^{1'}$–$R^{3'}$. Examples of preferred polymers include the following:

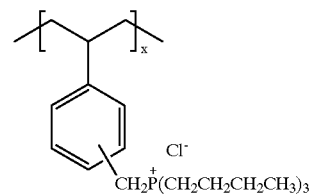

polyvinylbenzyltributyl phosphonium chloride

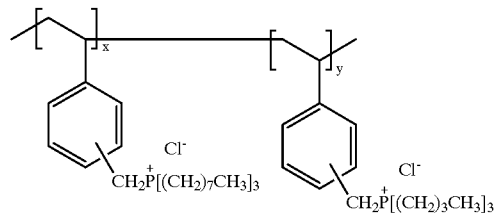

polyvinylbenzyltrioctyl phosphonium chloride-co-polyvinylbenzyltributyl phosphonium chloride

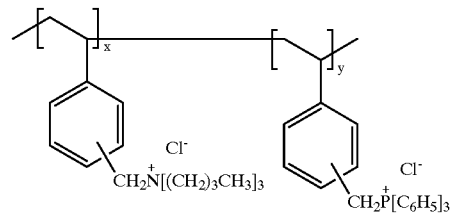

polyvinylbenzyltributyl ammonium chloride-co-polyvinylbenzyltriphenyl phosphonium chloride

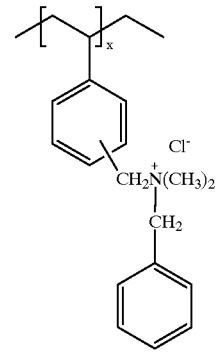

polyvinylbenzylbenzyldimethyl ammonium chloride

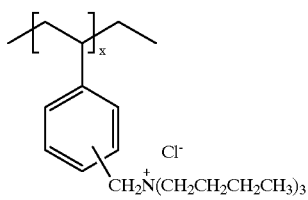

polyvinylbenzyltributylammonium chloride

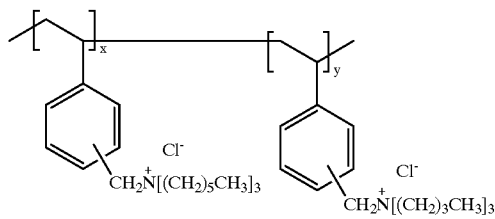

polyvinylbenzyltrihexyl ammonium chloride-co-polyvinylbenzyl tributyl ammonium chloride (THQ-TBQ)

These vinylbenzyl quaternary ammonium salt polymers can be prepared by free radical polymerization of the appropriate precursor monomers or by exhaustive alkylation of the corresponding tertiary amines or phosphines with polyvinylbenzyl chloride, or copolymers containing a pendant benzyl chloride function. This same approach can be taken using other polymeric alkylating agents such as chloromethylated polyphenylene oxide or polyepichlorohydrin. The same polymeric alkylating agents can be used as initiators of oxazoline ring-opening polymerization, which, after hydrolysis, yields polyethyleneimine graft copolymers. Such copolymers can then be quaternized, preferably with aralkyl groups, to give the final polymer.

Water soluble acetals of the polyvinylalcohol and a formylbenzyl quaternary salt, having the formula

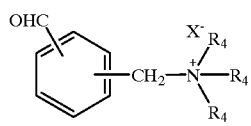

III wherein each $R_4$ is the same or a different aliphatic substituent and $X_1$ is an anion, as disclosed and claimed in Bronstein-Bonte et al U.S. Pat. No. 4,124,388, can also be used in practicing this invention. And, the individual vinylbenzyl quaternary ammonium salt monomers used to prepare the poly(vinylbenzyl quaternary ammonium salts) of formula I above can also be copolymerized with other ethylenically unsaturated monomers having no quaternary ammonium functionality, to give polymers such as those disclosed and claimed in Land et al U.S. Pat. No. 4,322,489; Bronstein-Bonte et al U.S. Pat. No. 4,340,522; Land et al U.S. Pat. No. 4,424,326; Bronstein-Bonte U.S. Pat. No. 4,503,138; Bronstein-Bonte U.S. Pat. No. 4,563,411; and Cohen et al U.S. Pat. No. 3,898,088, all of which polymers can also be used as enhancer substances in practicing this invention. Preferably these quaternized polymers will have molecular weights within the ranges given above for the poly(vinylbenzyl quaternary ammonium salts) of Formula I.

As it will be apparent to one skilled in the art, the use of cationic microgels or crosslinked latices are more suitable for the direct formation of cast membranes, but can also be used for the overcoating of preformed membranes. Such materials are well known as photographic mordants and may be synthesized using a monomer mixture which contains a crosslinking moiety substituted with two ethylenically unsaturated groups. Quaternary ammonium or phosphonium salt containing latices can be prepared using methodologies described in Campbell et al U.S. Pat. No. 3,958,995.

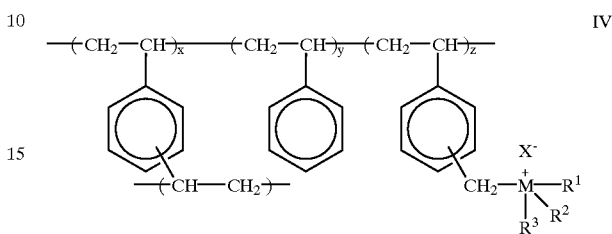

IV

Formula IV generally represents a useful subset of such water-soluble latex copolymers wherein the symbols $X^-$, $R^1$, $R^2$ and $R^3$ are as described above. The symbols X, Y and Z are mole fractions which must add together to give unity.

Preferably, a polymeric enhancer such as BDMQ is added to the enzyme or enzyme conjugate biological substance sources in an amount of 0.01 to 26% (0.1 to 250 mg/ml), more preferably 0.025 to 15% (25 to 150 mg/ml). Most preferably, BDMQ is added in an amount of 0.1 to 0.2% (1 to 2 mg/ml).

The emitted signal resulting from the dephosphorylated AttoPhos™ is by way of an energy transfer excitation from the excited state dioxetane dense fragment. The emitted signal can be captured on a green sensitive film or in a luminometer, CCD camera. The amount of emission detected will be responsive both to the presence of the biopolymer, and to the amount of the surface-bound biopolymer. The amount of biological substance is a function of the intensity of the emission.

The methods and the kits of the present invention can be used to determine the presence or concentration of any biological substance, including RNA, DNA, proteins and haptens. Further, the methods and kits of the present invention can be used for detections performed on membranes such as Western, Southern, Northern blotting and DNA sequencing, and can also be used for solution-phase assays. In the solution-based assay or when enhancing polymers are employed, they may require the dephosphorylated products of both AttoPhos™ and 1,2-dioxetane substrates, and thereby increasing the proximity between the donor and acceptor moieties.

EXAMPLES

Example 1

Western Blotting on Nitrocellulose and PVDP (detection of proteins IgG on membranes imaged on Photometrics Star 1 CCD camera).

Dilutions of rabbit IgG were electrophoresed on a 10% polyacrylamide gel using standard, known methods. The IgG samples were 200, 66.7, 22.2, 7.4 and 2.4 ng per lane for nitrocellulose and 100, 33.3, 11.1, 3.7 and 1.2 ng per lane for PVDF. The protein was then transferred to the membrane as follows: the gel was equilibrated in transfer buffer (5 mM MOPS, 2 mM sodium acetate, 20% methanol, pH 7.5) and then electrotransferred to nitrocellulose (Schleicher and Schuell BAS85) or PVDF (Tropix) at 90 volts for 1 hour at 4° C.

After transfer, the membranes were rinsed with phosphate buffered saline (PBS), blocked with 0.2% casein, 0.1% Tween-20 in PBS(blocking buffer), incubated for 30 minutes with a 1–10,000 dilution of alkaline phosphatase conjugated goat anti-rabbit antibody (GAR-AP) in blocking buffer, the PVDF membranes were washed twice for 5 minutes in blocking buffer, the nitrocellulose membranes were washed twice in 0.1% Tween-20 in PBS, all membranes were washed twice for 5 minutes in 0.1 M diethanolamine, 1 mM $MgCl_2$, pH 10 (substrate buffer), incubated for 5 minutes in a 1–20 dilution of Nitro-Block™ (Tropix) in substrate buffer, washed twice for 5 minutes in substrate buffer, incubated for 5 minutes in 0.25 mM CSPD® in substrate buffer and AttoPhos™ under various conditions, sealed in a plastic report cover, incubated for approximately 1 hour and imaged for 5 minutes with a Star I CCD camera (Photometrics).

Chemiluminescent images were obtained by integration of the chemiluminescent signal for 5 minutes with a Star I CCD camera interfaced to an Apple Macintosh IIci computer using IPLab Spectrum software. The CCD images were transferred into the NIH Image software package, and average and maximum pixel intensities were measured for each band.

Figure 3:
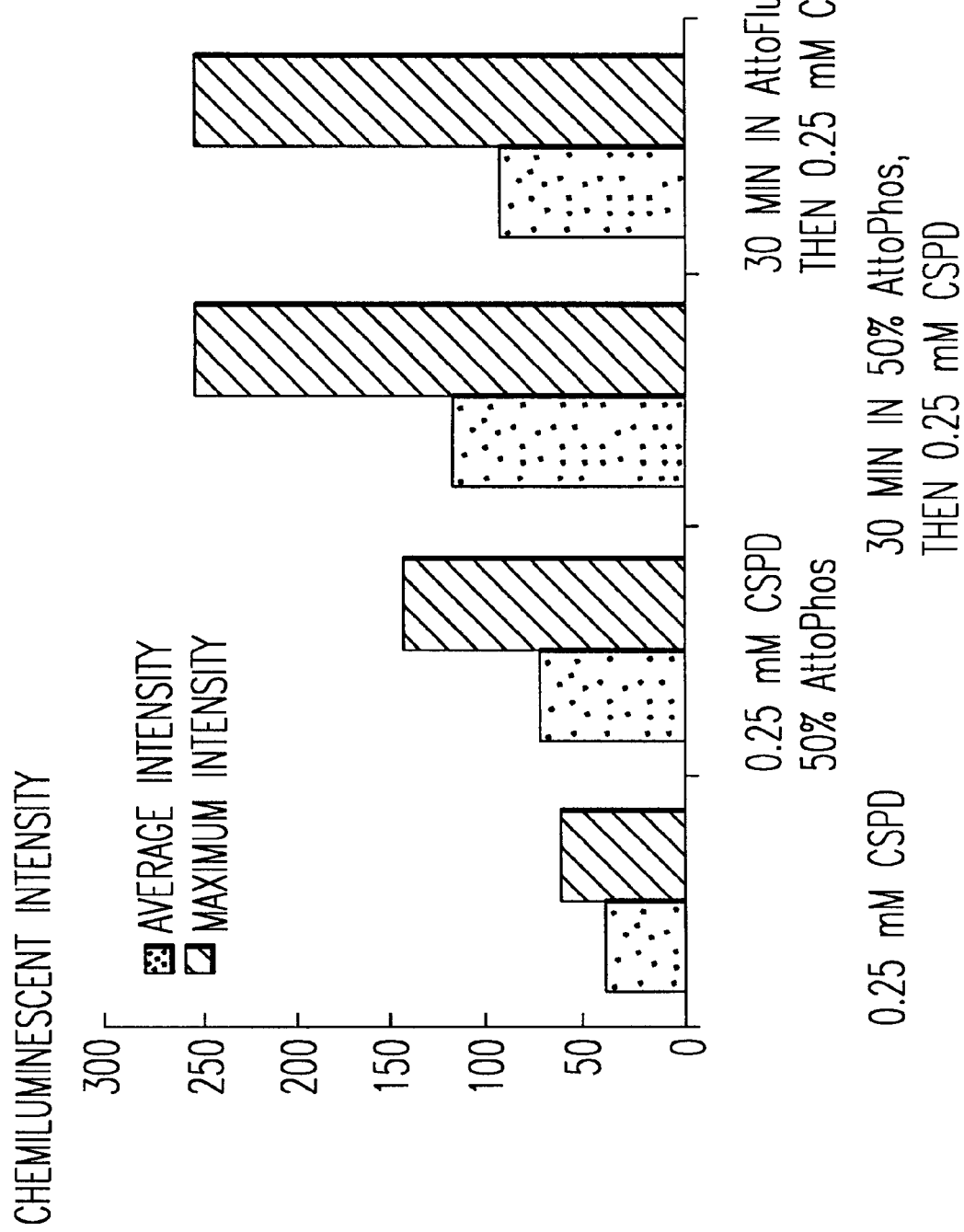
Figure 4A:
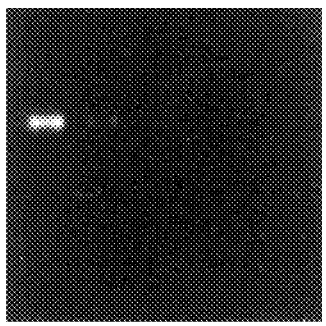
Figure 4B:
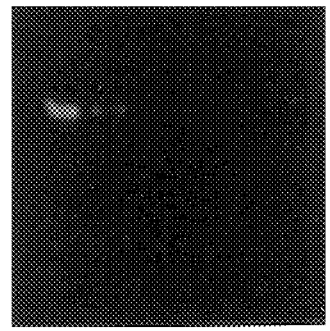
Figure 4C:
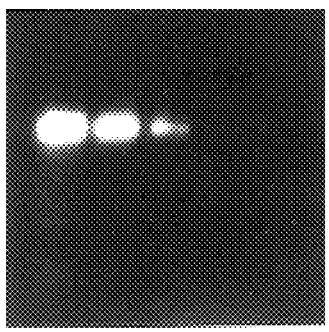
Figure 4D:
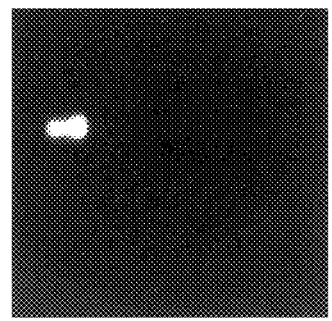
Figure 5:
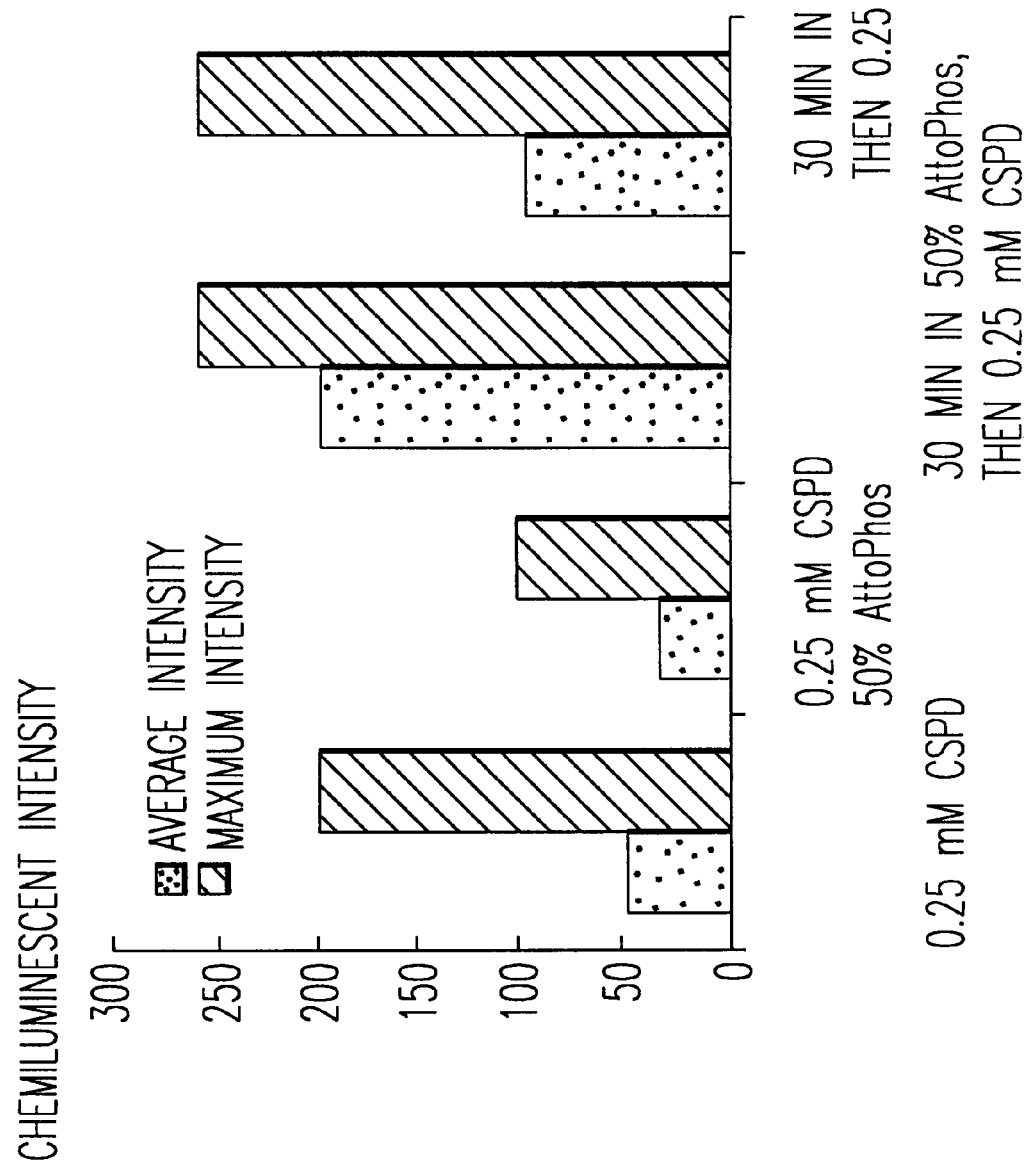

The CCD images, shown in FIGS. 2 and 4, are composites of the Western blot images. Blot A was incubated in 0.25 mM CSPD® in substrate buffer. Blot B was incubated in 0.25 mM CSPD® and 50% AttoPhos™ (50% AttoPhos™ buffer) simultaneously. Blot C was incubated first in 50% AttoPhos™ (50% substrate buffer) for 30 minutes, the AttoPhos™ was removed, the membrane was washed twice for 5 minutes in substrate buffer, and 0.25 mM CSPD® in substrate buffer was added. Blot D was incubated for 30 minutes with undiluted AttoFluor standard, then the membrane was washed twice for 5 minutes in substrate buffer followed by 0.25 mM CSPD® in substrate buffer. Images were obtained approximately 1 hour after the initial addition of CSPD®. The average and maximum signal intensities were plotted for the top dilution for each of the conditions described above as shown in FIGS. 3 and 5.

The results shown in FIGS. 2–5 demonstrate that maximum in tensity is obtained by the addition of AttoPhos™ followed by subsequent addition of the 1,2-dioxetane after a set period of time.

Example 2
PSA Immunoassay [Hybritech Prostate Specific Antigen (PSA)].

The standards from a Hybritech Tandem-E PSA kit (catalog #4823) were quantitated using the protocol and reagents supplied by the manufacturer, except for the detection step. The assay was performed as follows. An amount of 100 μL of each standard was aliquoted into 12×75 mm glass tubes (6 triplicates of the zero and triplicates of the other standards). An amount of 100 μL of the alkaline phosphatase conjugated mouse anti-PSA was added to each tube followed by one bead with attached capture anti-PSA antibody. The tube s were then incubated for 2 hours at room temperature on a shaking platform at 170 RPM. The beads were washed three times with 2 mL of Hybritech wash solution and once with 0.1 M diethanolamine, 1 $MgCl_2$, pH 10 (substrate buffer). Substrate was then added to each tube. The following three substrate compositions (200 μL per tube) were tested: 0.25 mM CSPD, 1 mg/mL BDMQ in substrate buffer added at time zero; 0.25 mM CSPD, 1 mg/mL BDMQ, 50% AttoPhos™ in substrate buffer added at time zero; 50% AttoPhos™, 1 mg/mL BDMQ in substrate buffer for 30 minutes followed by the addition of CSPD® (final concentration 0.25 mM). The chemiluminescent signal was measured 25 minutes after the addition of CSPD® (or CSPD®/AttoPhos™ mixture) with a Berthold 952T luminometer.

Figure 6A:
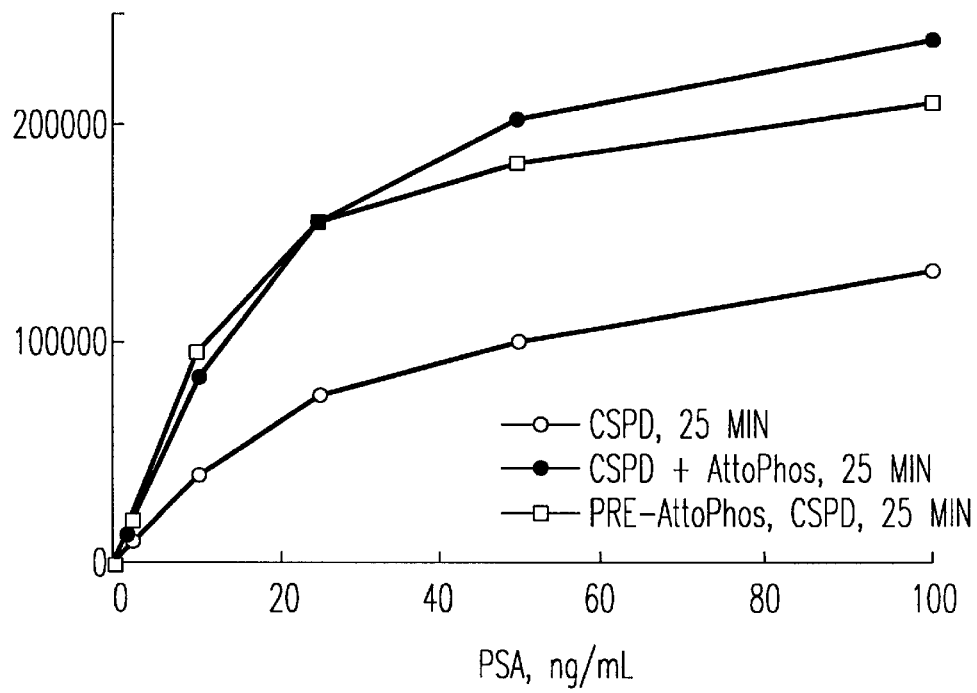
Figure 6B:
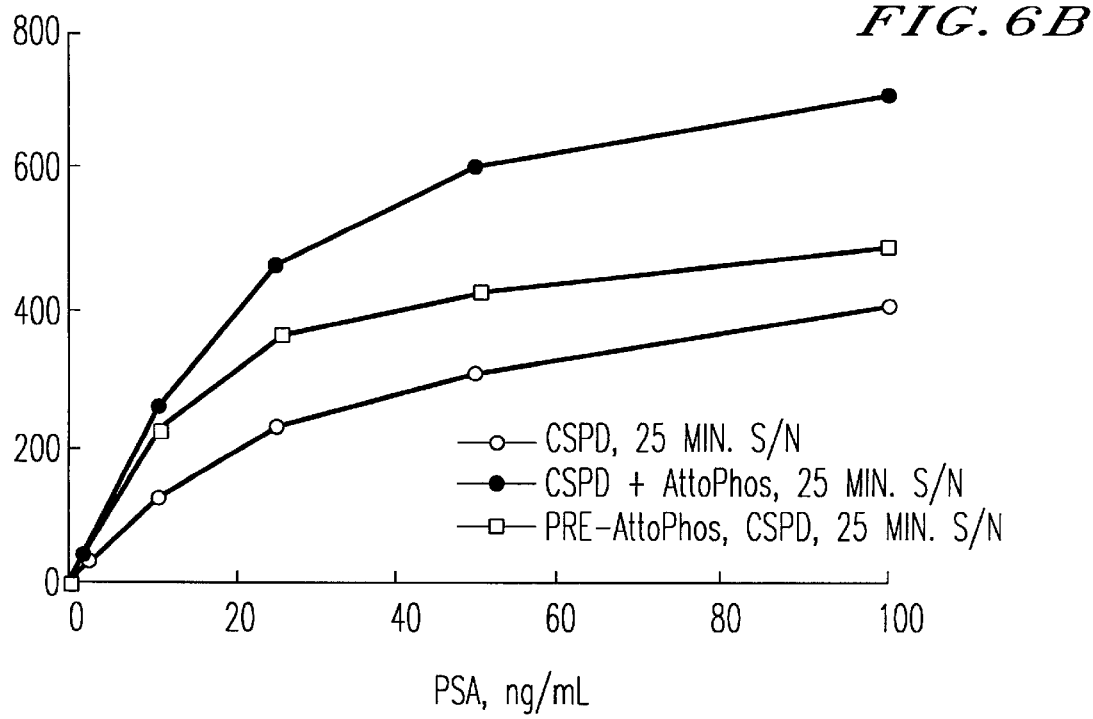

FIGS. 6 (A) and (B) demonstrate that both the signal and signal/noise ratios are greater with CSPD® and AttoPhos™ than with CSPD® alone. Therefore, increased signal was the result of use of CSPD® in connection with AttoPhos™.

Example 3
Solution Energy Transfer (energy transfer between the dephosphorylated AttoPhos™ and the dephosphorylated CSPD®).

The following is a list of the samples used for the Spex emission spectra. For all samples, 0.1 M diethanolamine, 1 mM $MgCl_2$, pH 10 was used to adjust the final volume to 2 ml. 100% Sapphire™ is equivalent to 10.0 mg/ml BDMQ.

Figure 7:
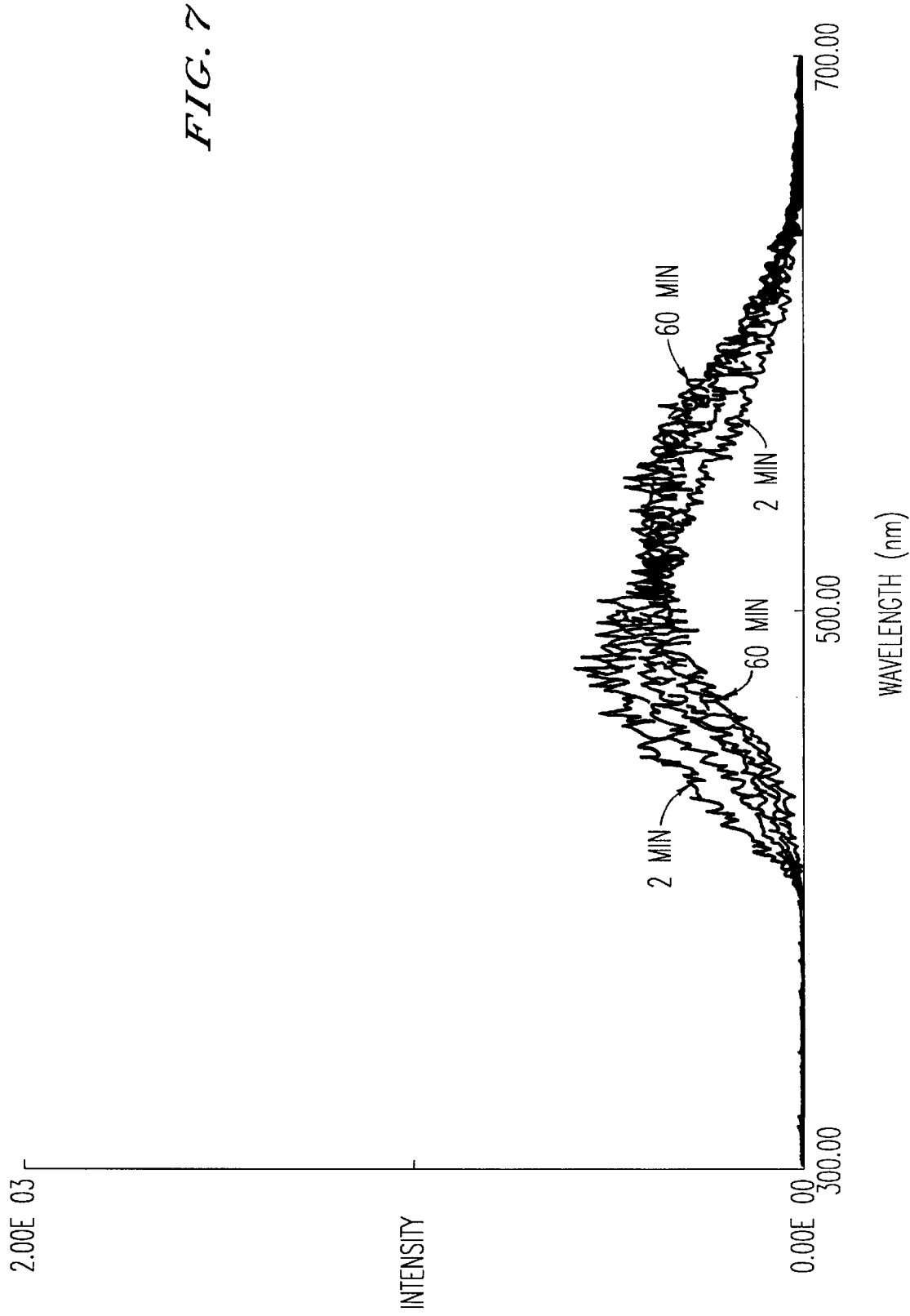
FIG. 7 is a chemiluminescent emission spectrum (intensity v. wavelength) obtained with 0.25 mM CSPD, 50% AttoPhos™, and alkaline phosphatase, as described in Example 3.
Figure 8:
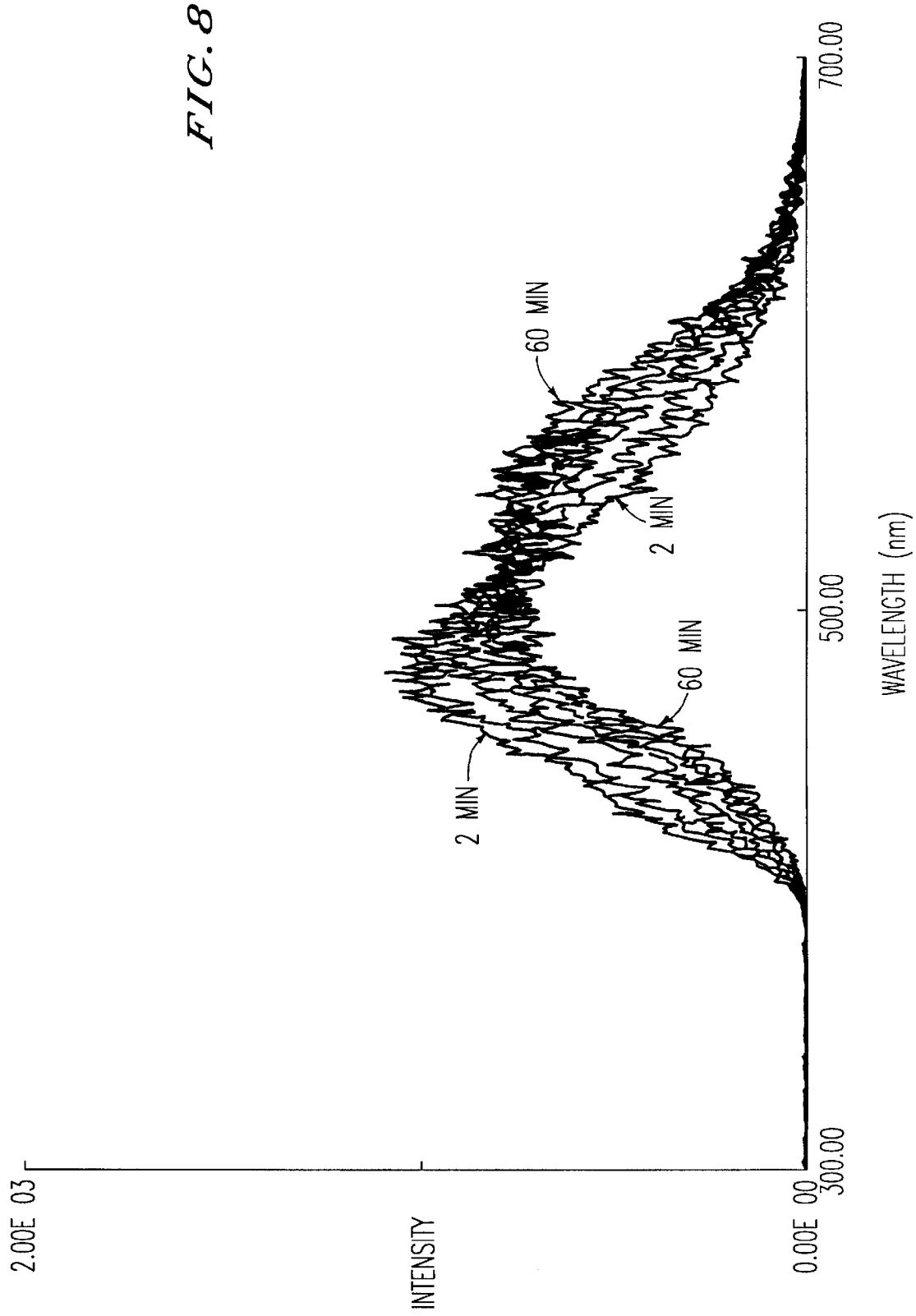
FIG. 8 is a chemiluminescence spectrum (intensity v. wavelength) obtained with 1.0 mM CSPD®, 50% AttoPhos™, and alkaline phosphatase, as described in Example 3.
Figure 9:
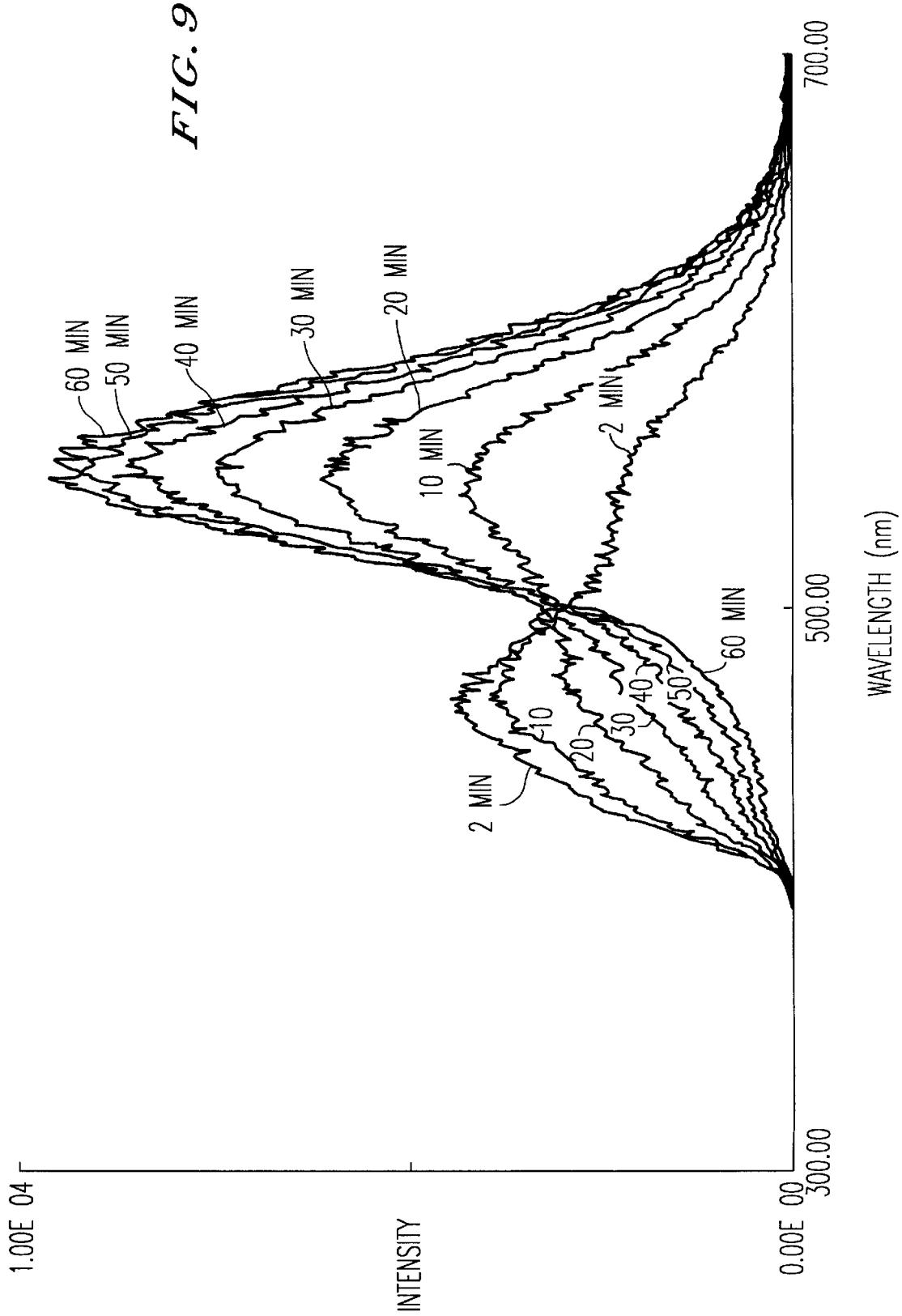
FIG. 9 is a chemiluminescence spectrum (intensity v. wavelength) obtained with 0.1 mM CSPD®, 50% AttoPhos™, 20% BDMQ, and alkaline phosphatase, as described in Example 3.
Figure 10:
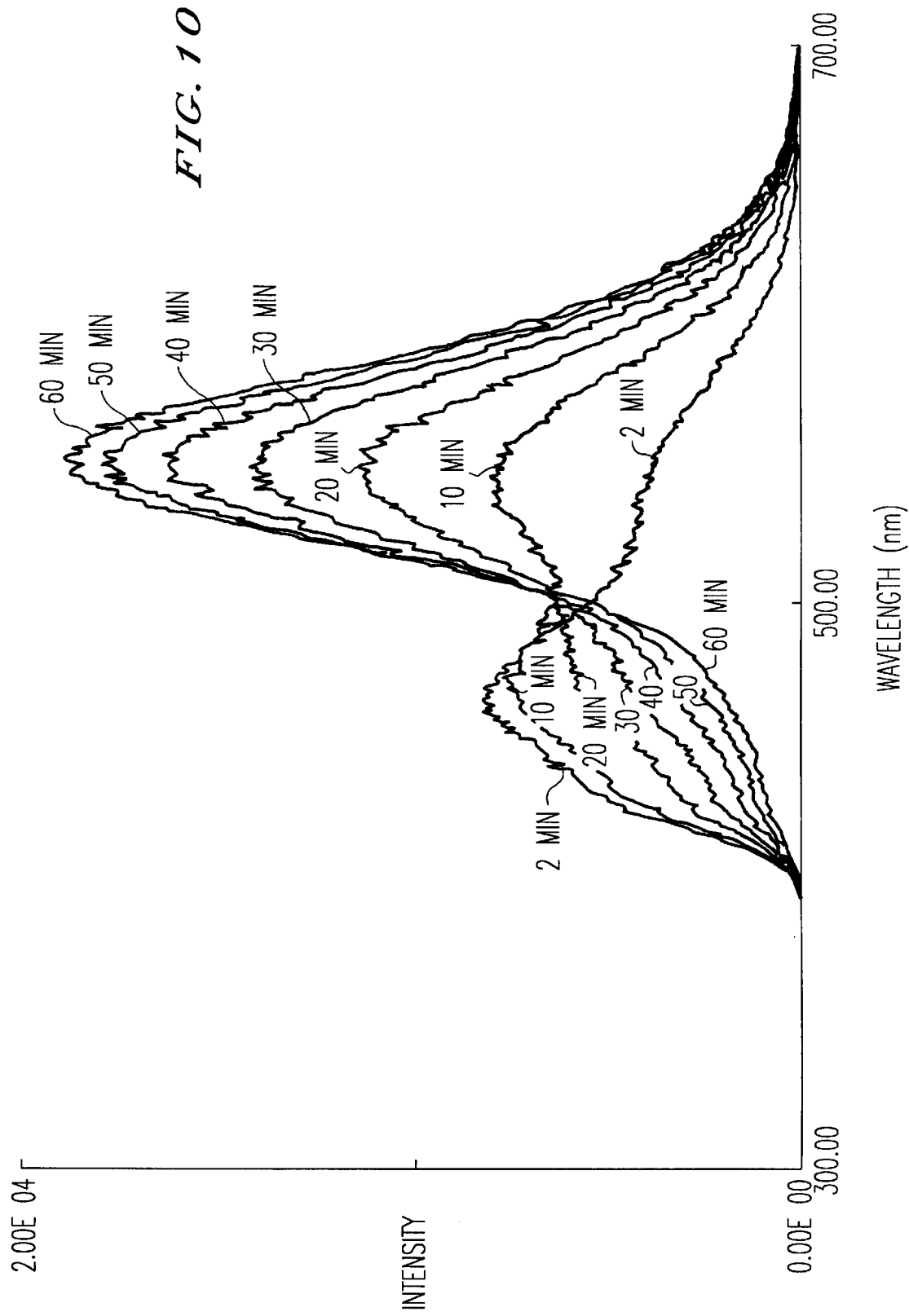
FIG. 10 is a chemiluminescence spectrum (intensity v. wavelength) obtained with 0.25 mM CSPD®, 50% AttoPhos™, 20% BDMQ, and alkaline phosphatase, as described in Example 3.
Figure 11:
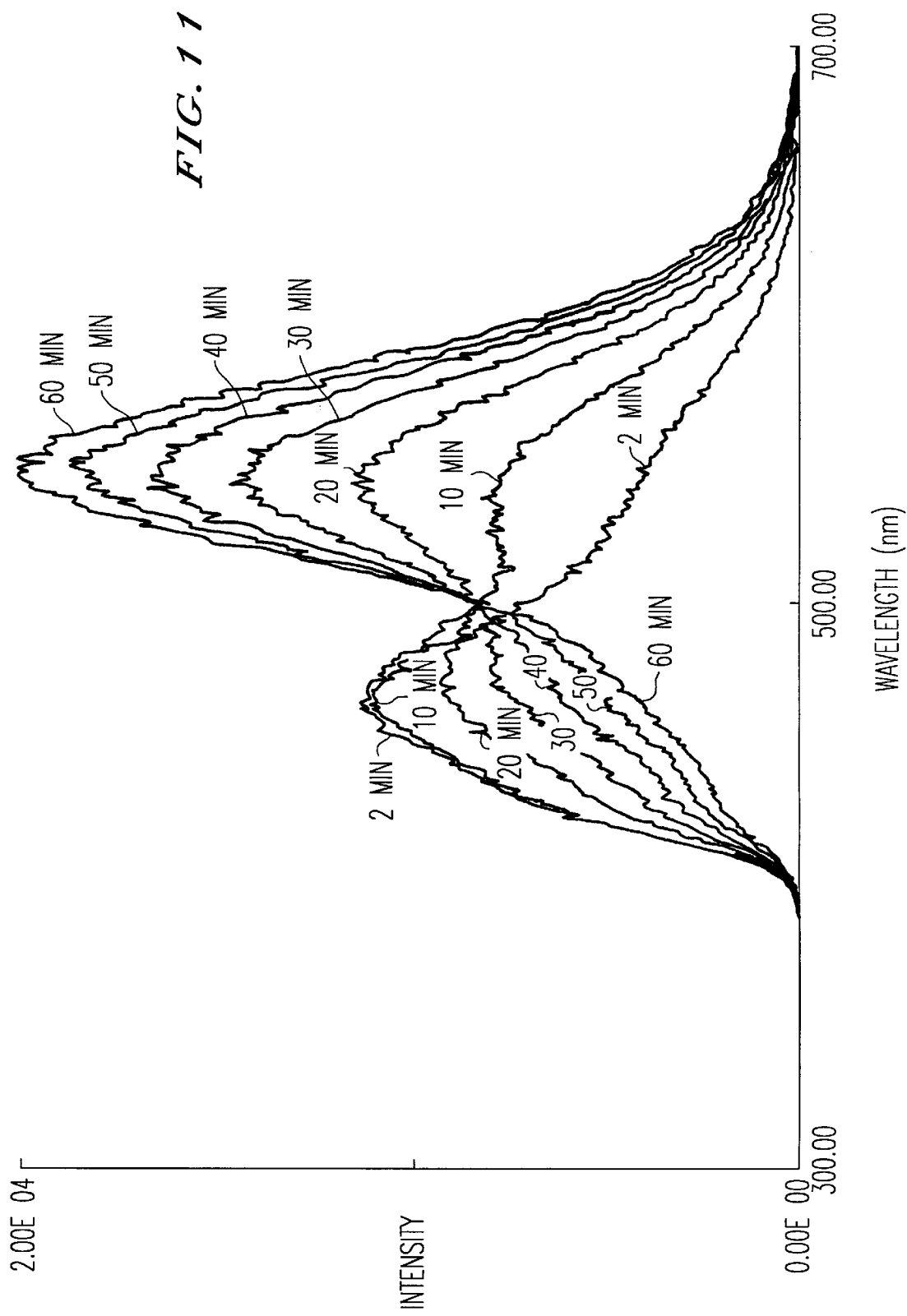
FIG. 11 is a chemiluminescence spectrum (intensity v. wavelength) obtained with 0.5 mM CSPD®, 50% AttoPhos™, 20% BDMQ, and alkaline phosphatase, as described in Example 3.
Figure 12:
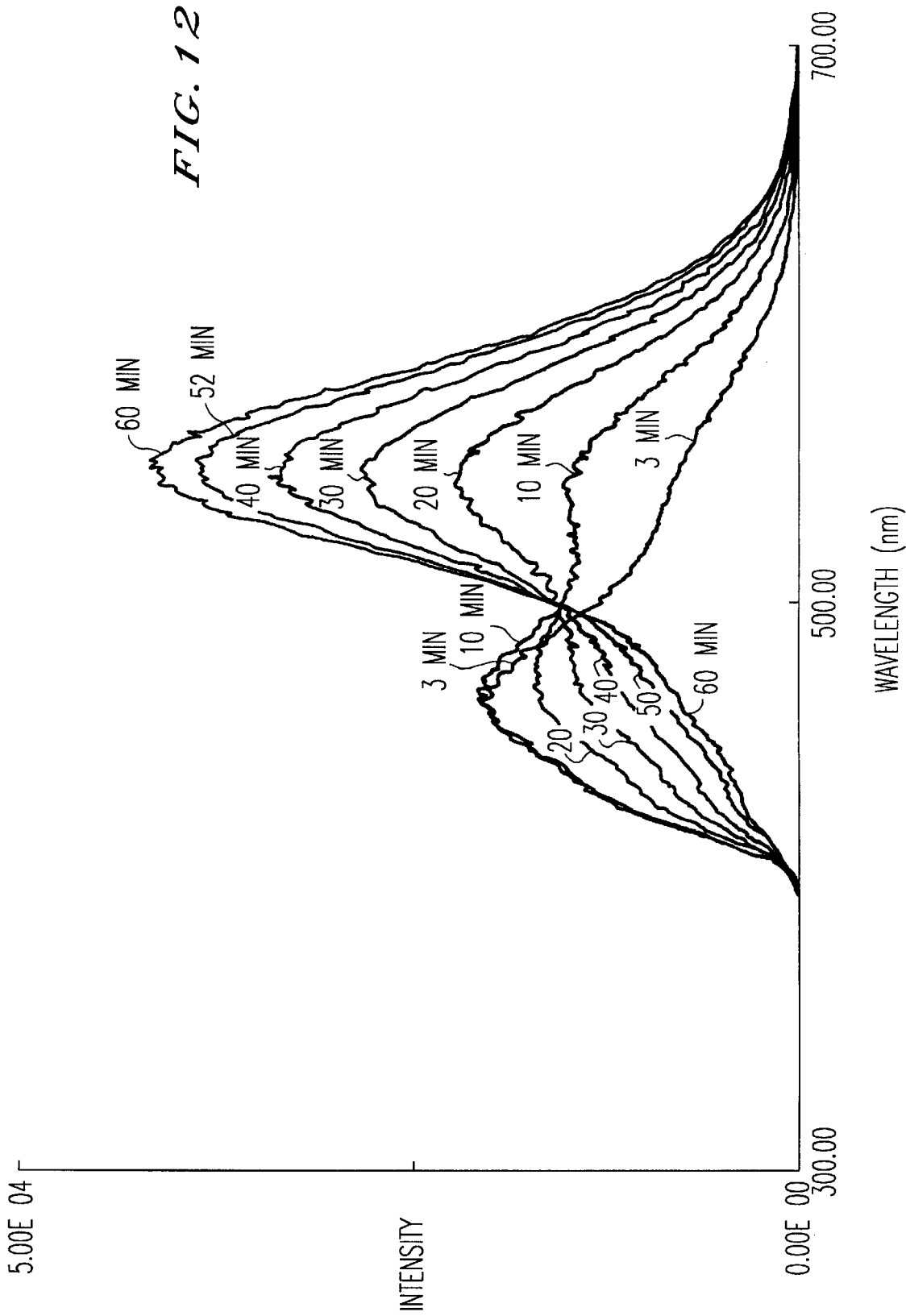
FIG. 12 is a chemiluminescence spectrum (intensity v. wavelength) obtained with 1.0 mM CSPD®, 50% AttoPhos™, 20% BDMQ, and alkaline phosphatase, as described in Example 3.
Figure 13:
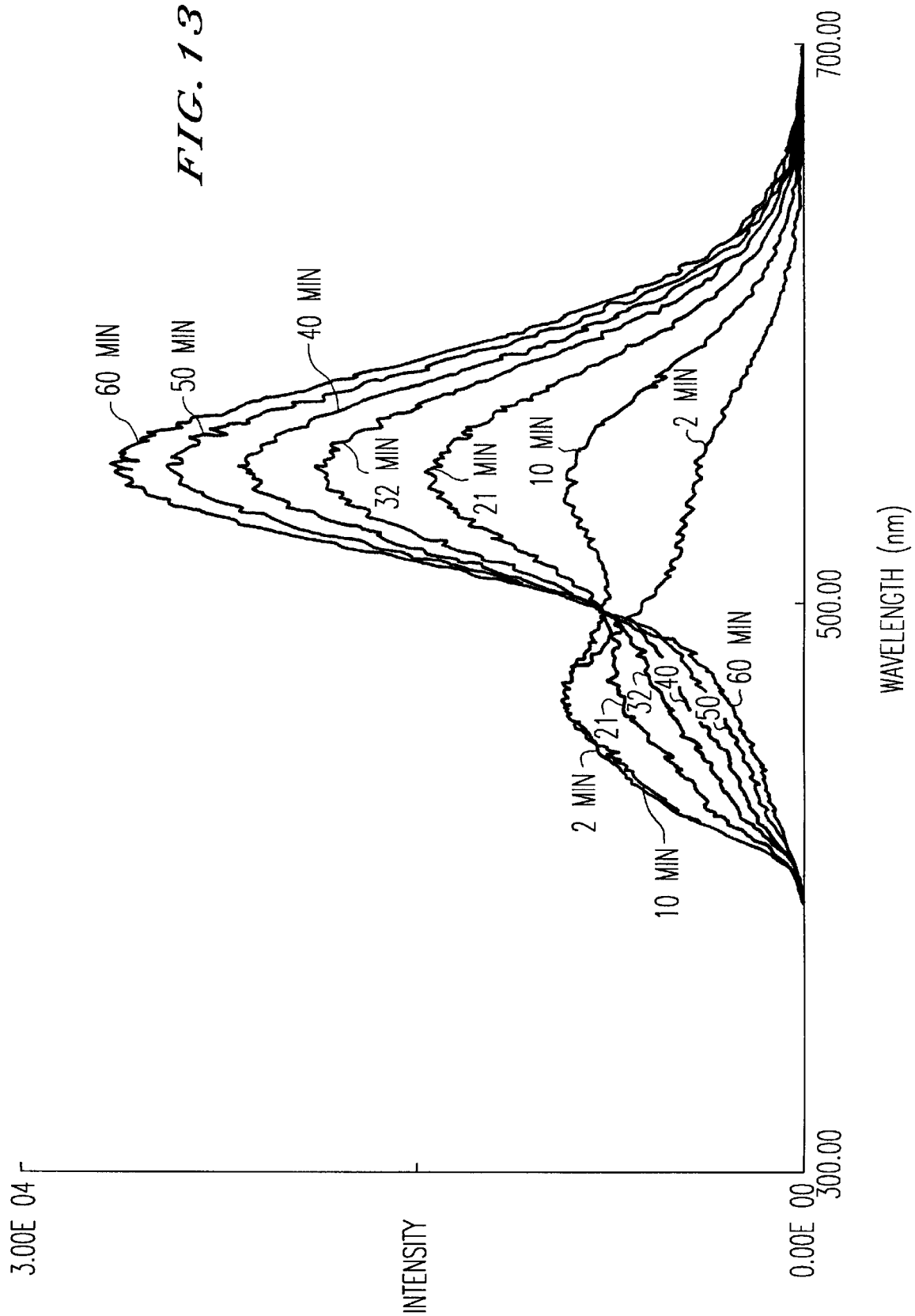
FIG. 13 is a chemiluminescence spectrum (intensity v. wavelength) obtained with 1.0 mM CSPD®, 50% AttoPhos™, 10% BDMQ, and alkaline phosphatase, as described in Example 3.
Figure 14:
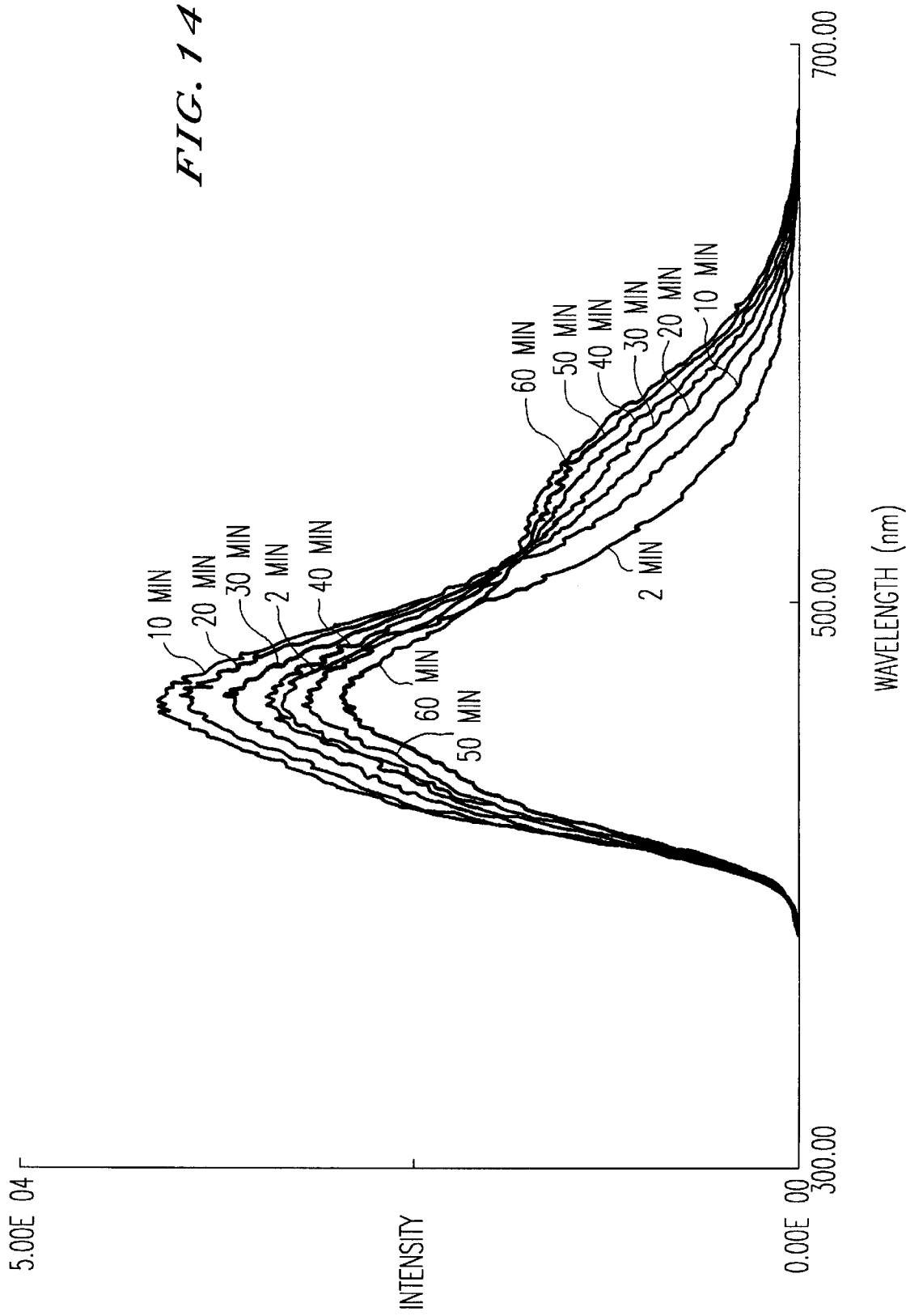
FIG. 14 is a chemiluminescence spectrum (intensity v. wavelength) obtained with 1.0 mM CSPD®, 10% AttoPhos™, 20% BDMQ, and alkaline phosphatase, as described in Example 3.
Figure 15:
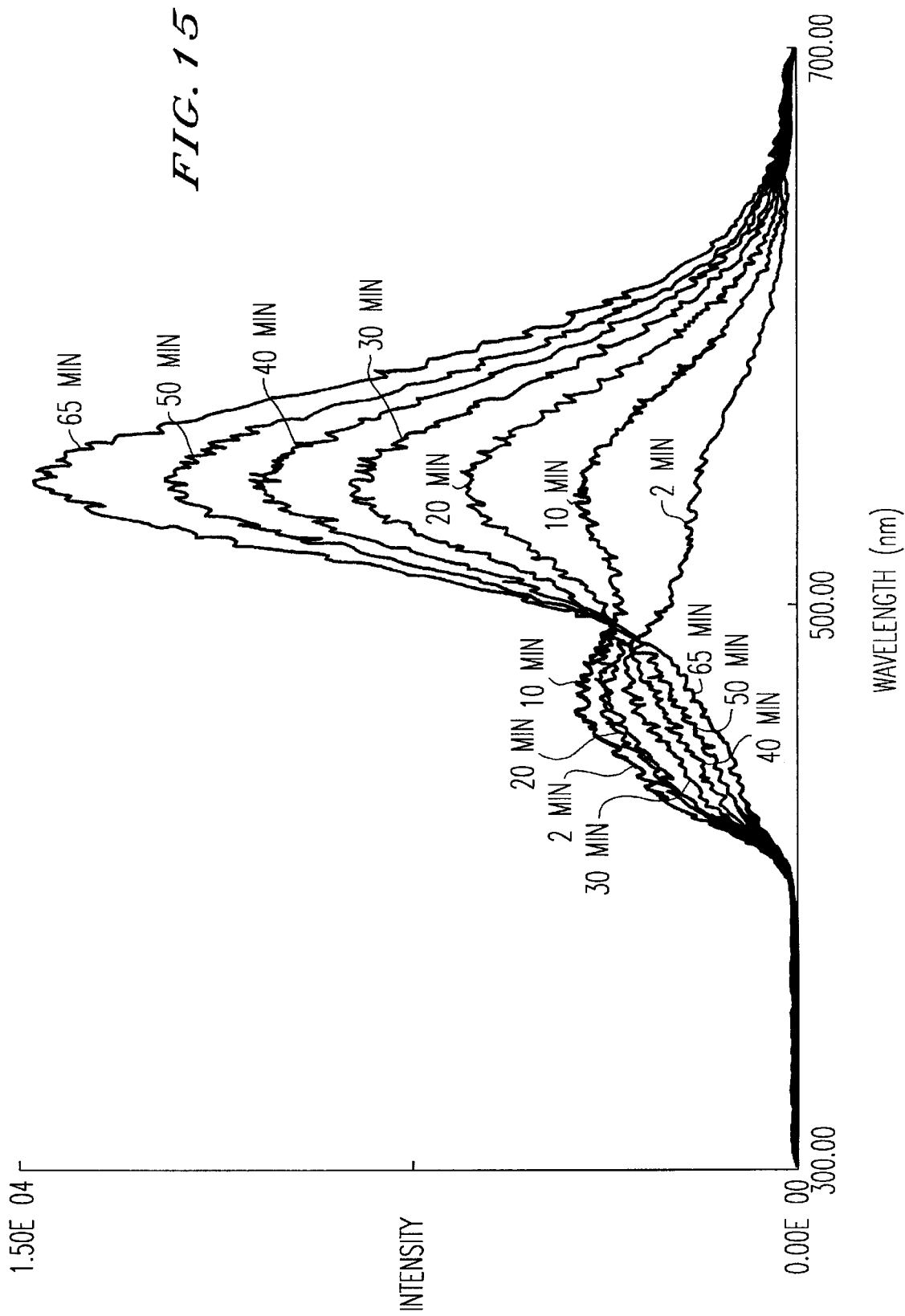
FIG. 15 is a chemiluminescent emission spectrum (intensity v. wavelength) obtained using 1.0 mM CSPD®, 50% AttoPhos™, 2.0 mg/ml polyvinylbenzyltriphenyl phosphonium chloride-co-polyvinylbenzylenzyldimethyl ammonium chloride (40 mole % TPP/60 mole % BDMQ), and alkaline phosphatase as described in Example 3.
Figure 16:
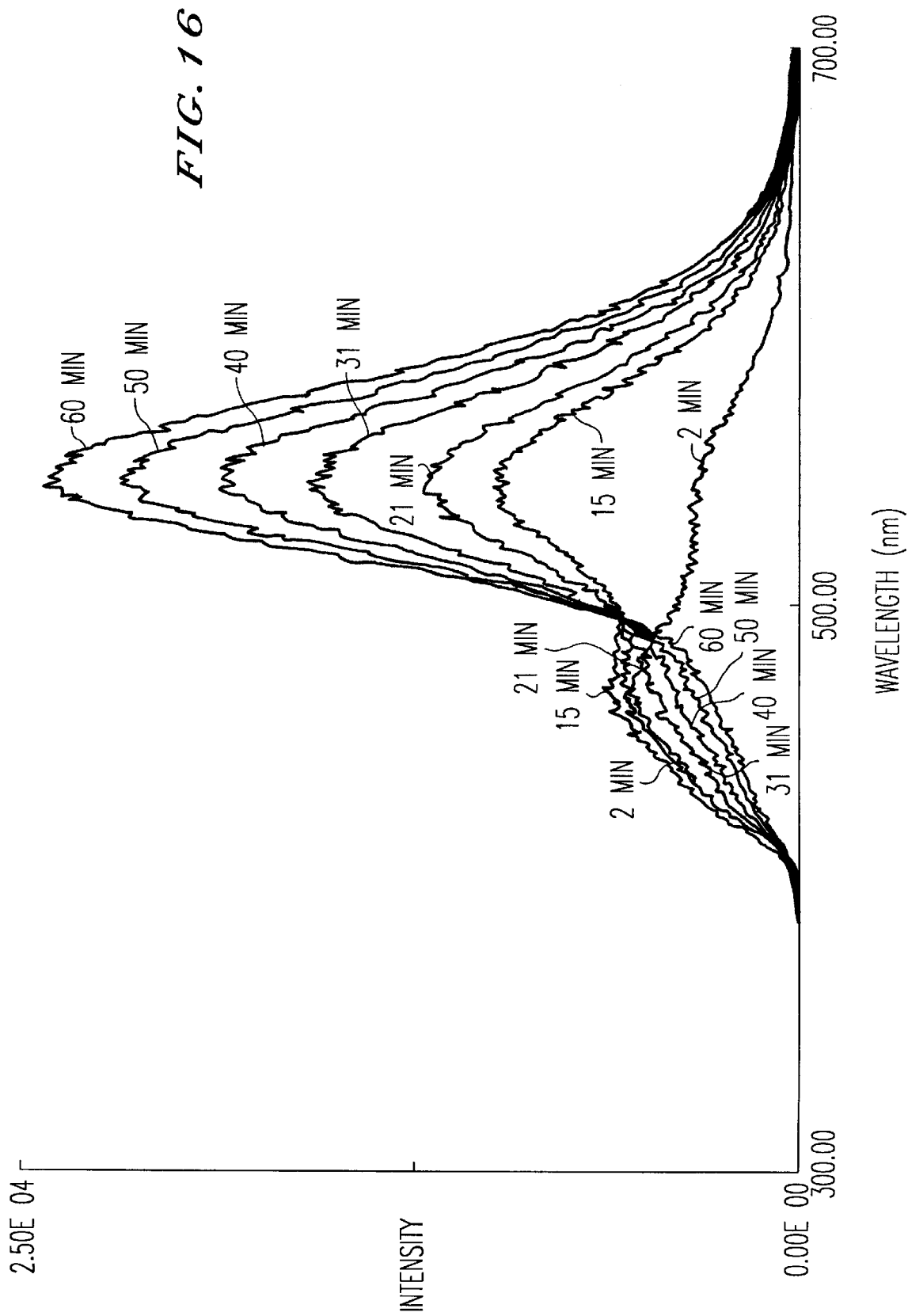
FIG. 16 is a chemiluminescent emission spectrum (intensity vs. wavelength) obtained using 1.0 mM CSPD®, 50% AttoPhos™, 2.0 mg/ml polyvinylbenzyltriphenyl phosponium chloride-co-polyvinylbenzyltributyl ammonium chloride (45 mole % TPP/55 mole % TBQ), and alkaline phosphatase as described in Example 3.
Figure 17:
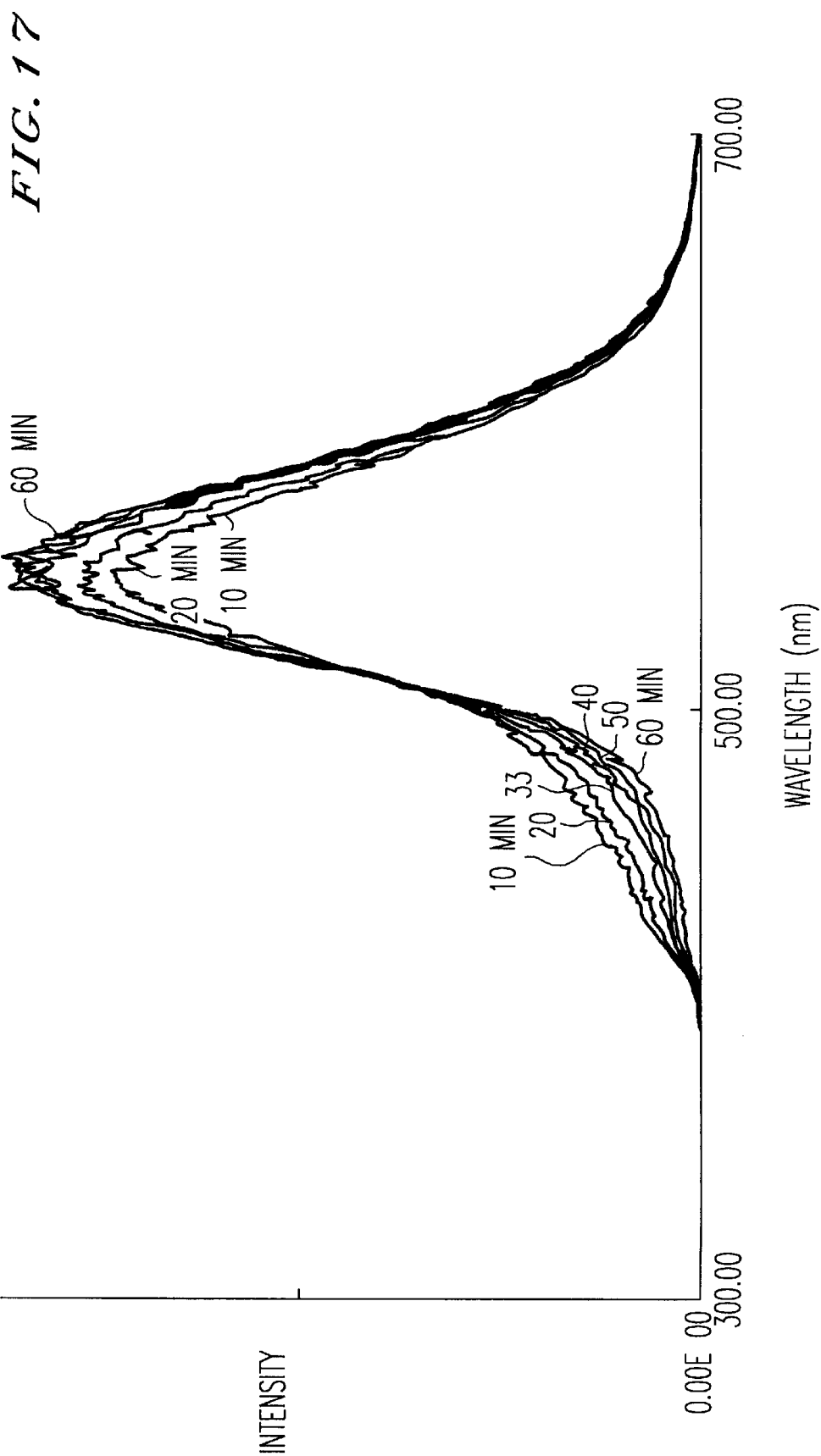
FIG. 17 is a chemiluminescent emission spectrum (intensity vs. wavelength) obtained using a 30 minute preincubation of alkaline phosphatase in 50% AttoPhos™, 20% BDMQ, followed by the addition of CSPD (0.25 mM final concentration) at time zero as described in Example 3.
Figure 18:
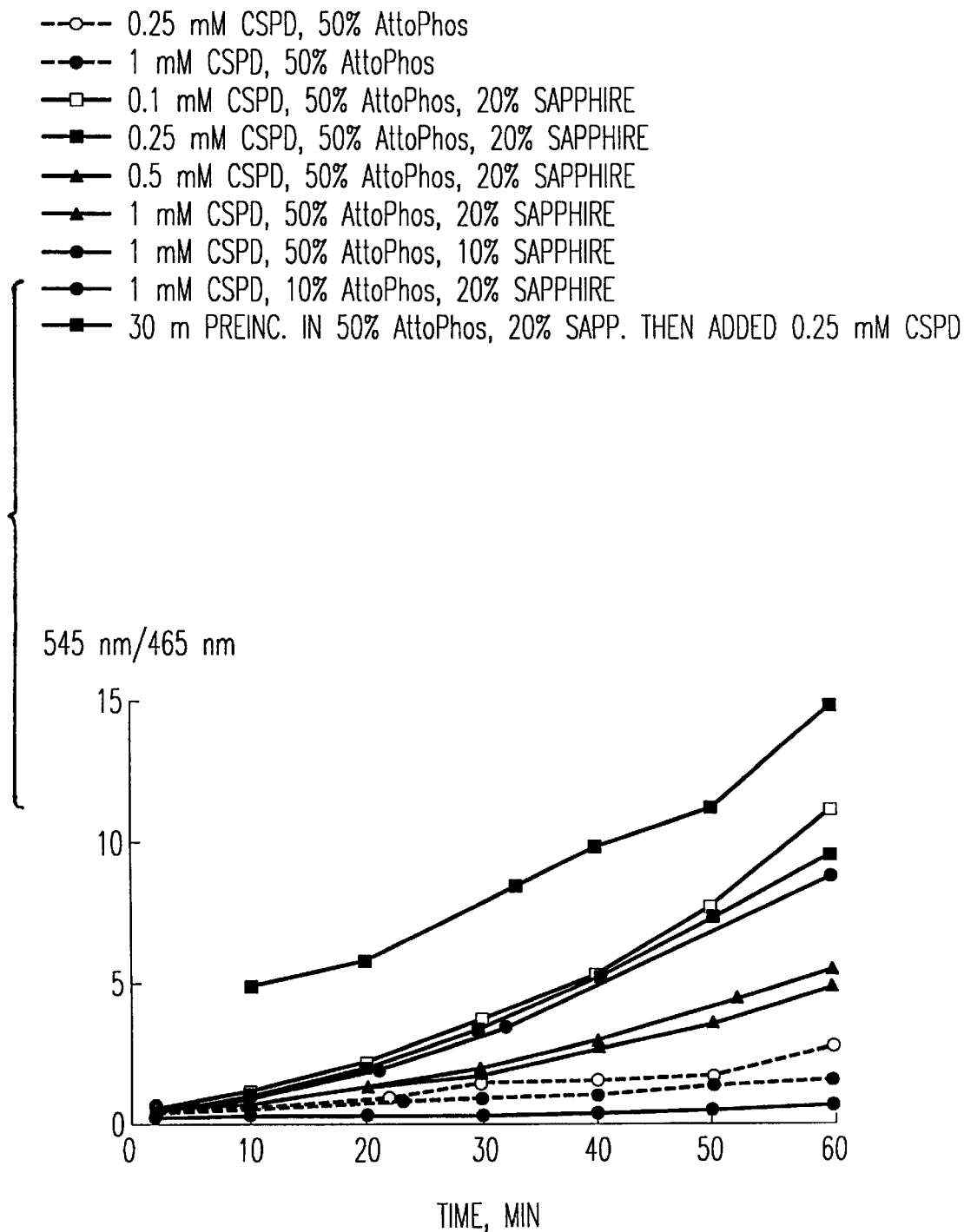
FIG. 18 is a graph showing the ratio of emission at 545 nm/465 nm obtained from the data in FIGS. 7–14 and FIG. 17.
Figure 19:
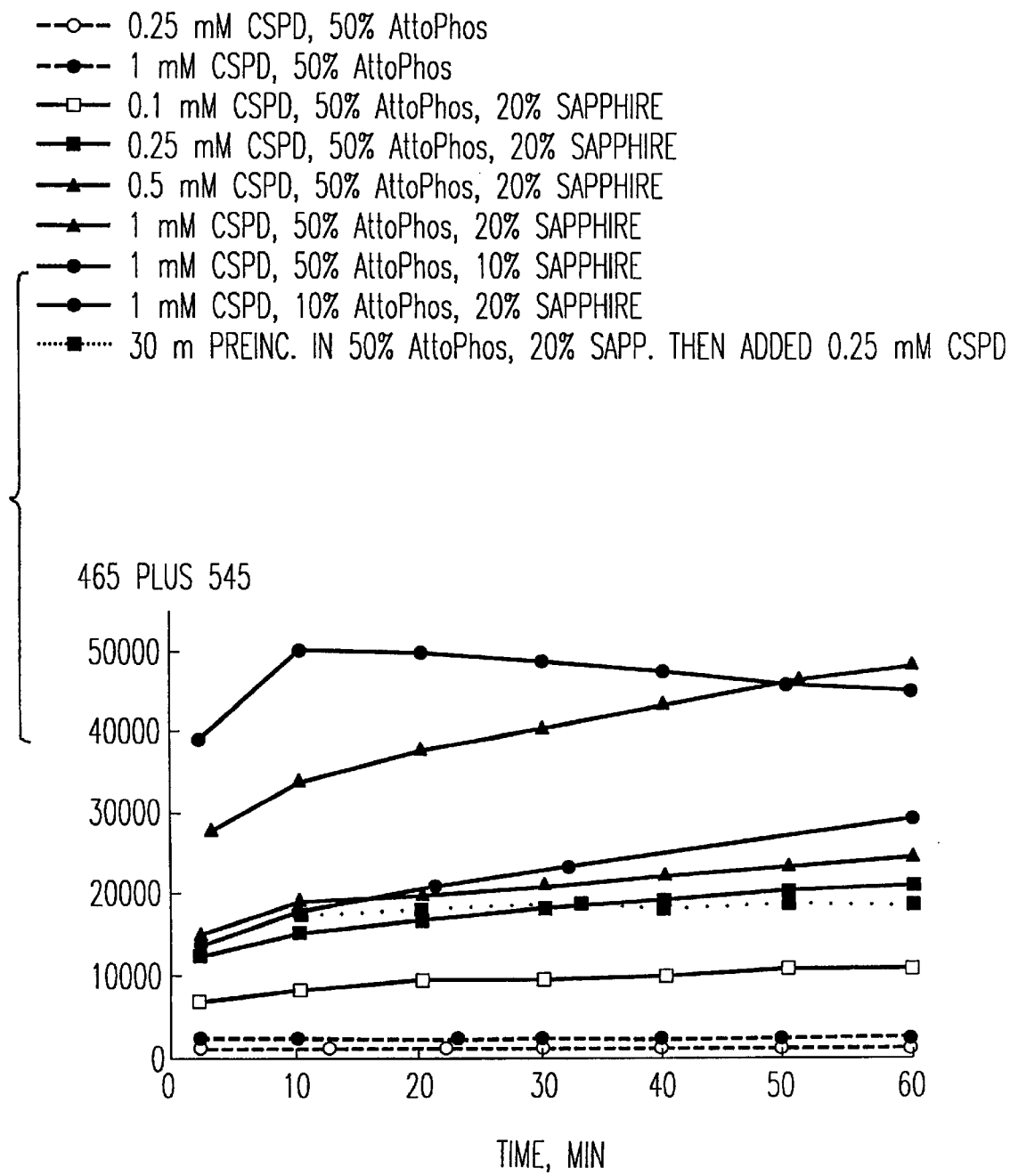
FIG. 19 is a graph showing the sum of emission at 465 nm and 545 nm, obtained from the data in FIGS. 7–14 and FIG. 17.
Figure 20:
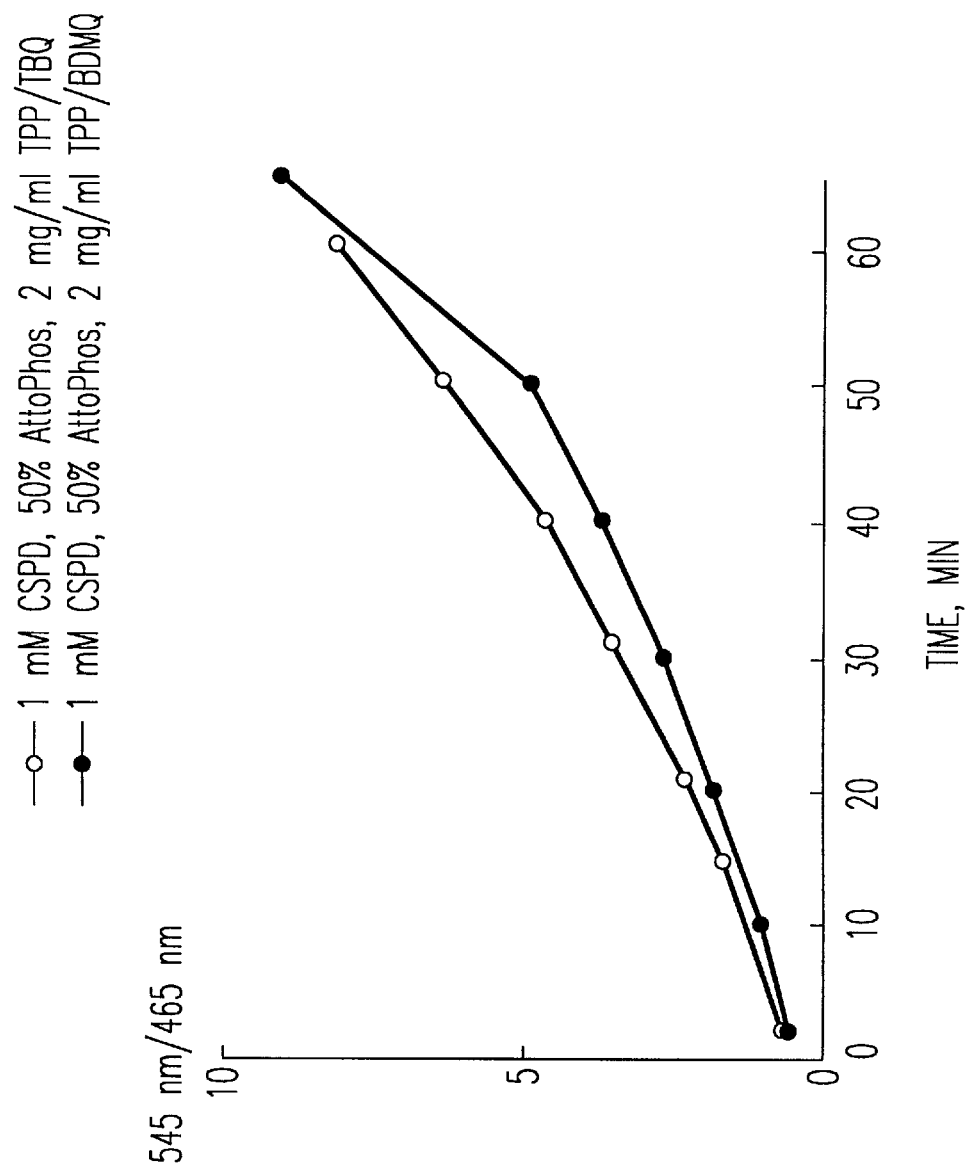
FIG. 20 is a graph showing the ratio of emission at 545 nm/465 nm obtained from the data in FIGS. 15 and 16.
Figure 21:
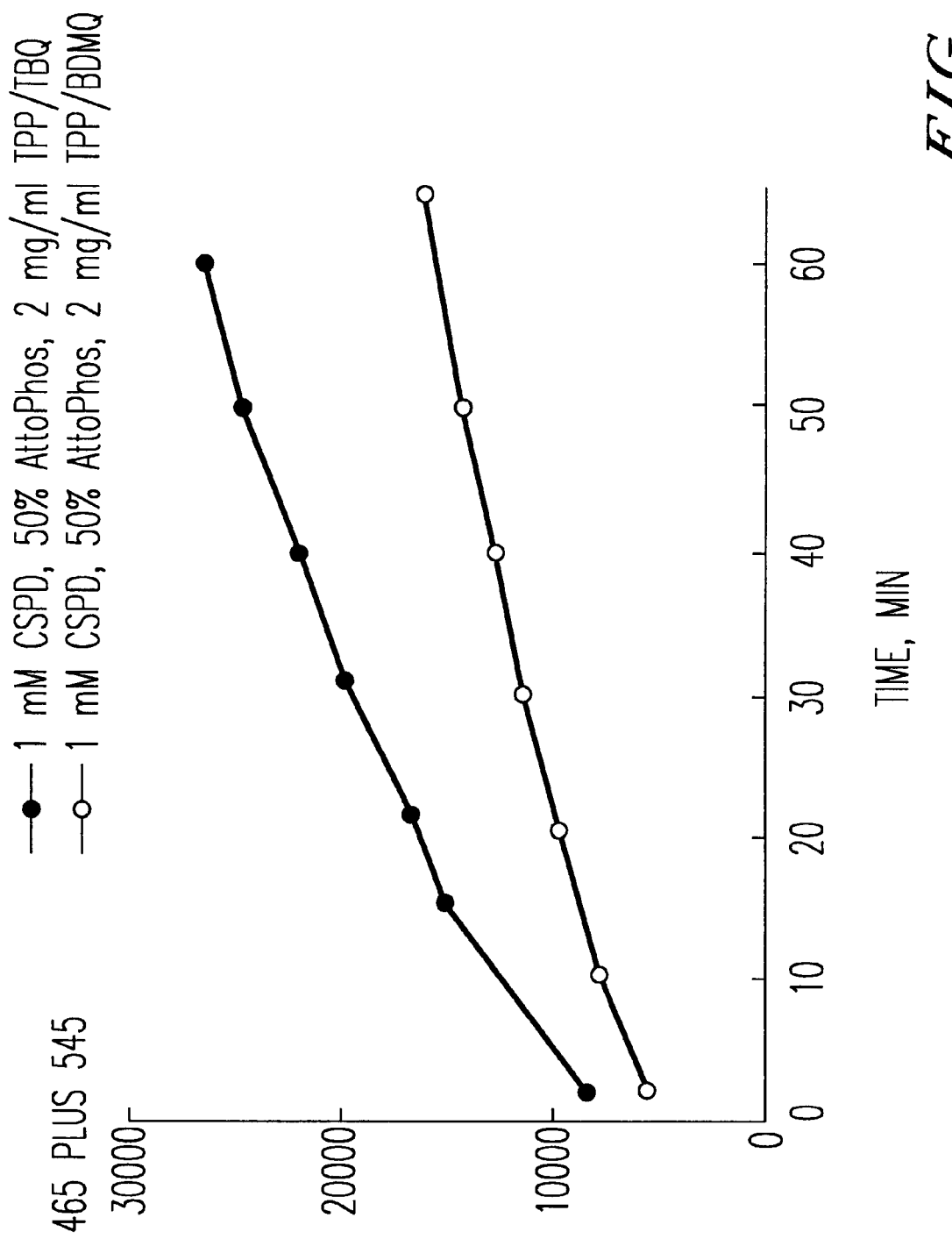
FIG. 21 is a graph showing the sum of emission at 465 nm and 545 nm, obtained from the data in FIGS. 15 and 16.

| | | |
|---|---|---|
| 1. | FIG. 7 | 0.25 mM CSPD ®, 50% AttoPhos ™ |
| 2. | FIG. 8 | 1.0 mM CSPD ®, 50% AttoPhos ™ |
| 3. | FIG. 9 | 0.1 mM CSPD ®, 50% AttoPhos ™, 20% BDMQ |
| 4. | FIG. 10 | 0.25 mM CSPD ®, 50% AttoPhos ™, 20% BDMQ |
| 5. | FIG. 11 | 0.5 mM CSPD ®, 50% AttoPhos ™, 20% BDMQ |
| 6. | FIG. 12 | 1.0 mM CSPD ®, 50% AttoPhos ™, 20% BDMQ |
| 7. | FIG. 13 | 1.0 mM CSPD ®, 50% AttoPhos ™, 10% BDMQ |
| 8. | FIG. 14 | 1.0 mM CSPD ®, 10% AttoPhos ™, 20% BDMQ |
| 9. | FIG. 15 | 1.0 mM CSPD ® 50% AttoPhos ™, 2.0 mg/ml TPP(0.4)/BDMQ 0.6) |
| 10. | FIG. 16 | 1.0 mM CSPD ® 50% AttoPhos ™, 2.0 mg/ml TPP(0.45)/TBQ(0.55) |
| 11. | FIG. 17 | a 30 minute preincubation of alkaline phosphatase in 50% AttoPhos ™, 20% BDMQ, followed by the addition of CSPD ® (0.25 mM final concentration) at time zero |

At time=0, alkaline phosphatase was added to each sample (final concentration, $1.12 \times 10^{-11}$ M) and the cuvette was inserted into the fluorimeter (Spex Fluorolog). Emission spectra were obtained with the monochrometer slits set at 10 mm and signal was integrated for 0.5 seconds per nm. Spectra were recorded at 2, 10, 20, 30, 40, 50 and 60 minutes, in most cases.

The results are shown in FIGS. 7–21.

This set of experiments shows energy transfer from CSPD to Attophos™ in a buffer. Such solution-based assays are used with immunoassays which are performed in buffers. FIGS. 7–21 demonstrate that there is an energy transfer between the dephosphorylated emitter of CSPD® and the dephosphorylated AttoPhos™. FIGS. 9–17 further show that this energy transfer is greatly improved by the presence of enhancing polymers. FIGS. 7 and 8 demonstrate that an increase in the donor, dephosphorylated CSPD® emitter increases the signal via energy transfer, i.e., the Atto emission. In this case, the blue emission (CSPD® chemiluminescence) increases. This may be due to a population of the methyl-meta-oxybenzoate anion (CSPD® emitter) which is not within the energy transfer distance from the Atto acceptor. FIG. 14 demonstrates that the green signal originates from Atto, because when the concentration of AttoPhos™ is low, the energy transfer signal is also very low. FIG. 12 shows that the relative energy transfer signal when the substrates are added sequentially, i.e., first adding AttoPhos™ which becomes dephosphorylation creating the ground state emitter, followed by CSPD® addition which upon dephosphorylanon, fragments and, generates the excited state donor which transfers its energy to the accumulated acceptor from the dephosphorylated AttoPhos™.

Example 4

Detection of Biotinylated DNA

Biotinylated DNA was detected by binding streptavidin alkaline phosphatase, and then subsequently incubating with either CSPD® 1,2-dioxetane substrate for alkaline phosphatase or mixtures of CSPD® the fluorescent alkaline phosphatase substrate AttoPhos™. Specifically, biotinylated 35mer was spotted on to Pall Biodyne A nylon membrane, 210 pg in the top spot followed by successive 1:3 dilutions. DNA was detected by performing the Tropix Southern-Light™ procedure up to the substrate incubation step. Each membrane was then individually incubated with a different substrate solution as follows:

1) 0.25 mM CSPD® in assay buffer (0.1M DEA pH 10, 1 mM $MgCl_2$),
2) 50% AttoPhos™ solution; 50% 1 mM CSPD® in assay buffer,
3) 50% AttoPhos™ solution; 50% 0.25 mM CSPD® in assay buffer,
4) 1 mM CSPD® in AttoPhos™ solution,
5) membrane coated with dephosphorylated AttoPhos™ and then incubated with 0.25 mM CSPD® in assay buffer,
6) AttoPhos™ solution.

The image was obtained using a Photometrics Star 1 CCD Camera in a light-tight box without any external light source.

Figure 22:
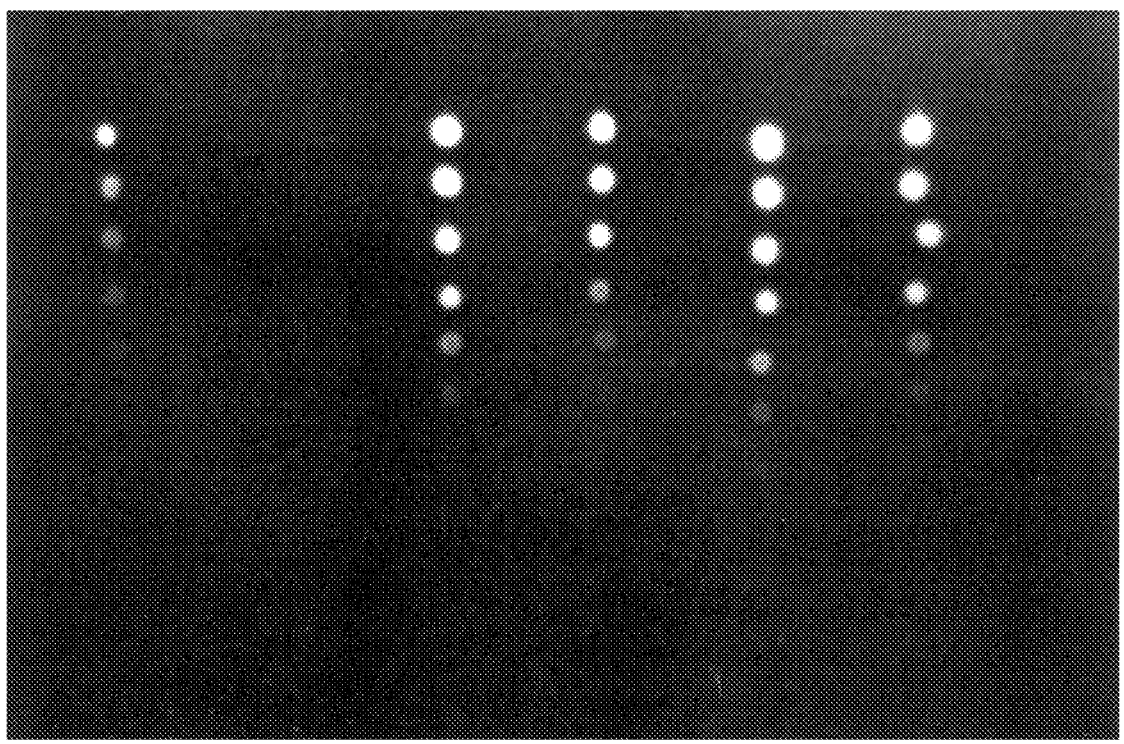
FIG. 22 is a CCD camera image detecting the presence of biotinylated DNA.

FIG. 22 shows an increased light signal from the samples of AttoPhos™ in combination with CSPD®.

Applicants have endeavored to illustrate their invention by extensive embodiment of possible combinations. Nonetheless, it is recognized that the possible combinations are endless, and cannot be exhaustively embodied. Given the above teaching, those of ordinary skill in the art will arrive at enhancement agents and additives not specifically exemplified in the foregoing application. The examples are not intended to be limiting, and the identification of other combinations, given the foregoing disclosure, is well within the skill of those practicing this technology without undue experimentation. Such combinations are intended to be within the scope of the invention, save as expressly limited or excluded by the claims set forth below.

What is claimed is:

1. A method for generating fluorescence emission to detect the presence of a biological substance in a biological sample, said method comprising the steps of:
   a) forming an enzyme complex by binding an enzyme to said substance;
   b) adding a hydrophobic fluorescent emitter and a 1,2-dioxetane to said complex;
   c) allowing said enzyme to cleave an enzyme-cleavable moiety on said 1,2-dioxetane using said enzyme to leave an excited state emitter oxyanion of the formula:

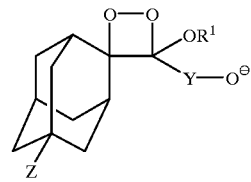

wherein Z is H, Cl or other halogens, an alkyl, a carboxy or an alkoxy; $R^1$ is a $C_1$–$C_{20}$ alkyl or a $C_{1\text{-}12}$ aryl or aralkyl; Y is a phenyl or naphthyl, unsubstituted or substituted with an electron donating or an electron withdrawing group; and
   d) segregating said hydrophobic fluorescent emitter and said dioxetane oxyanion into a hydrophobic region, wherein said hydrophobic fluorescent emitter and said dioxetane oxyanion are in close proximity such that energy released by said oxyanion on decomposition is transferred to said hydrophobic fluorescent emitter, causing said emitter to fluoresce.

2. The method of claim 1, wherein said hydrophobic fluorescent emitter and said oxyanion are in a liquid solution.

3. The method of claim 1, wherein both said hydrophobic fluorescent emitter and said dioxetane oxyanion are located on a surface used to perform said method.

4. The method of claim 1, wherein said method further comprises adding to said complex a signal enhancing agent, wherein said signal enhancing agent is a polymeric salt selected from the group consisting of ammonium, phosphonium, and sulphonium polymeric salts.

* * * * *